United States Patent
Hatt et al.

(10) Patent No.: US 9,809,593 B2
(45) Date of Patent: Nov. 7, 2017

(54) USE OF TETRAMIC ACID DERIVATIVES AS NEMATICIDES

(71) Applicant: Syngenta Participations AG, Basel (CH)

(72) Inventors: Fabienne Hatt, Basel (CH); Anke Buchholz, Stein (CH)

(73) Assignee: Syngenta Participations AG, Basel (CH)

( * ) Notice: Subject to any disclaimer, the term of this patent is extended or adjusted under 35 U.S.C. 154(b) by 0 days.

(21) Appl. No.: 14/891,788

(22) PCT Filed: May 21, 2014

(86) PCT No.: PCT/EP2014/060411
§ 371 (c)(1),
(2) Date: Nov. 17, 2015

(87) PCT Pub. No.: WO2014/191271
PCT Pub. Date: Apr. 12, 2014

(65) Prior Publication Data
US 2016/0090384 A1   Mar. 31, 2016

(30) Foreign Application Priority Data
May 28, 2013  (EP) .................................... 13169528

(51) Int. Cl.
| A01N 43/42 | (2006.01) |
| A61K 31/44 | (2006.01) |
| C07D 471/10 | (2006.01) |
| A01N 43/40 | (2006.01) |
| A01N 43/90 | (2006.01) |
| A01N 47/06 | (2006.01) |

(52) U.S. Cl.
CPC .......... *C07D 471/10* (2013.01); *A01N 43/40* (2013.01); *A01N 43/90* (2013.01); *A01N 47/06* (2013.01)

(58) Field of Classification Search
None
See application file for complete search history.

(56) References Cited

U.S. PATENT DOCUMENTS

| 8,415,369 B2 * | 4/2013 | Zambach ............... A01N 43/38 514/278 |
| 9,067,892 B2 * | 6/2015 | Muehlebach .......... A01N 43/90 |

FOREIGN PATENT DOCUMENTS

| EP | WO2009/049851 | * | 4/2009 | .......... C07D 211/94 |
| EP | 2127522 A1 | | 12/2009 | |
| EP | WO2010/063670 | * | 6/2010 | .......... C07D 471/10 |
| EP | WO2010/066780 | * | 6/2010 | .......... C07D 471/10 |
| EP | WO 2011/151247 | * | 12/2011 | .......... C07D 471/10 |
| WO | 2009/049851 A1 | | 4/2009 | |
| WO | 2009/085176 A2 | | 7/2009 | |
| WO | 2010/063670 A1 | | 6/2010 | |

OTHER PUBLICATIONS

International Search Report for International Patent Application No. PCT/EP2014/060411 mailed Jul. 8, 2014.

* cited by examiner

*Primary Examiner* — Jeffrey H Murray
(74) *Attorney, Agent, or Firm* — R. Kody Jones

(57) ABSTRACT

Use of a tetramic acid compound according to formula (I) or (I') with a second nematicide as a treatment for crop plants to combat and control nematodes in the soil of said crop plants.

5 Claims, No Drawings

USE OF TETRAMIC ACID DERIVATIVES AS NEMATICIDES

RELATED APPLICATION INFORMATION

The application is a 371 of International Application No. PCT/EP2014/060411, filed 21 May 2014, which claims priority to European Patent Application No. 13169528.0, filed 28 May 2013, the contents of all of which are incorporated herein by reference herein.

The present invention relates to the use of known tetramic acid derivatives for combating and controlling soil-dwelling, in particular phytoparasitic nematodes. Methods for reducing overall damage and losses in plant health, vigor and yield caused by plant parasitic nematodes are disclosed. In another embodiment, methods of treating plants to reduce nematode damage by applying a seed and/or soil treatment followed by a foliar treatment are described.

Nematodes are microscopic unsegmented worms known to reside in virtually every type of environment (terrestrial, freshwater, marine). Of the over 80,000 known species, many are agriculturally significant. One such species is the root knot nematode which attacks a broad range of plants, shrubs, and crops. These soil-born nematodes attack newly formed roots causing stunted growth, swelling or gall formation. The roots may then crack open thus exposing the roots to other microorganisms such as bacteria and fungi. With environmentally friendly practices such as reduced or no tillage farming, and various nematode species acquiring resistance to transgenic seed, nematode related crop loss appears to be on the rise.

Chemical nematicides such as soil fumigants or non-fumigants have been in use for many years to combat infestations. Such nematicides may require repeated applications of synthetic chemicals to the ground prior to or at planting. Due to their toxicity, chemical nematicides have come under scrutiny from the Environmental Protection Agency (EPA) and in some cases their use has been limited or restricted by the EPA. As the use of traditional chemical nematicides such as methyl-bromide and organophosphates continue to be phased out, a need for the development of alternative treatment options has arisen.

Damage to plant and crop yields by nematodes occurs throughout the growing season. Current practices treat the seeds prior to planting or treat the soil around the plant. Nematicides are typically not applied at later growth stages, especially as a foliar application, mainly due to the limited availability of suitable nematicides, the ineffectiveness of available nematicides and due to the crop injury incurred from the effective but highly toxic nematicides and/or undesirable residues that remain in the food-based harvested crops. Instead, farmers have relied on a plant-based resistance approach to inhibition of nematodes. This involves cultivating and breeding naturally-occurring strains/variants of crops that are innately more resistant and tolerant to nematodes. This feature is then selectively bred into various seed genetic lines.

While this has found some success, there is still significant crop loss due to nematode infestations during planting and growth stages. Unfortunately, nematode infestation is difficult to spot visually because the effects are not immediately obvious. It has also been difficult to diagnose nematode infestation by loss of yield.

Therefore, there remains a need for effective methods to reduce nematode infestation throughout the growing cycle.

It is already known that certain cyclic ketoenols have herbicidal, insecticidal and acaricidal properties. Known to have insecticidal and/or acaricidal action are derivatives disclosed in WO2009/049851, WO2010/066780 and WO2010/063670. Other compounds of this class are known to have nematicidal effect (WO2009/085176) and mixtures of such derivatives with other nematicidal compounds (WO2011/100424).

SUMMARY OF THE INVENTION

Surprisingly, it has now been determined that the compounds of the formulae (I)

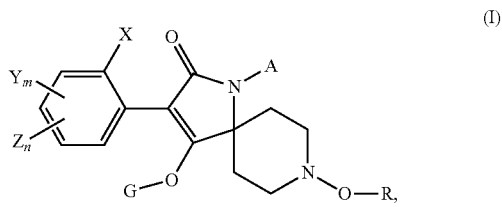

wherein
X, Y and Z independently of each other are methyl, ethyl, iso-propyl, n-propyl, methoxy, fluoro, bromo or chloro;
m and n, independently of each other, are 0, 1, 2 and m+n is 0, 1, 2;
G is hydrogen, or a latentiating group;
R is hydrogen, methyl, ethyl, iso-propyl, n-propyl, tert-butyl, sec-butyl, iso-butyl, or n-butyl;
A is hydrogen, methyl, ethyl, n-propyl, iso-propyl, methoxy, ethoxy, methoxymethyl, ethoxymethyl, methoxyethyl;
or an agrochemically acceptable salt or an N-oxide thereof;
and more preferably, the compounds of the formula (I) wherein,
X, Y and Z independently of each other are methyl, ethyl, fluoro, bromo or chloro;
m and n, independently of each other, are 0, 1, 2 and m+n is 1, 2;
G is hydrogen, or a latentiating group;
R is hydrogen, methyl or ethyl;
A is hydrogen, methyl, ethyl, methoxy, ethoxy;
or an agrochemically acceptable salt or an N-oxide thereof;
and most preferably, the compounds of the formula (I) wherein,
X, Y and Z independently of each other are methyl or chloro;
m and n, independently of each other, are 0, 1, 2 and m+n is 1, 2;
G is hydrogen, or a latentiating group;
R is hydrogen, methyl;
A is hydrogen, methyl, methoxy;
or an agrochemically acceptable salt or an N-oxide thereof;
can be used as a treatment on crop plants to combat and control nematodes in the soil of said crop plants i.e. used as a nematicide to protect crop plants. Preferably the treatment is a foliar treatment of said crop plants. In a preferred embodiment, the crops plants treated are in need of protection from nematodes, in particular phytoparasitic nematodes.

The compounds according to formula (I) can be used to reduce the population density of nematodes in the soil crop plants. Preferably the treatment is a foliar treatment of said crop plants.

The invention therefore covers a method for combating and controlling nematodes by (i) providing a compound according to formula (I) and
(ii) treating the crop attacked by nematodes or susceptible to attack by nematodes with a compound according to formula (I).

In a preferred embodiment, the plants treated are in need of protection from nematodes, in particular phytoparasitic nematodes.

Preferably, the compound provided is formulated and/or tankmixed with an adjuvant and/or diluted before being applied.

Preference is given to using the compound according to formula (I) for controlling phytoparasitic nematodes, more preferably in perennial crops or in annual crops.

Preference is given to using the compound according to formula (I) for controlling nematodes in perennial crops.

Preference is given to using the compound according to formula (I) for controlling nematodes in annual crops.

In another aspect the invention also relates to a method for reducing nematode damage to a plant which comprises
(i) treatment of a seed prior to planting and/or treatment of soil surrounding a planted seed or plant with a known nematicide
(ii) followed by treatment of the an aerial plant part of a plant obtained from the seed with a compound according to formula (I').

wherein the compound of formula (I') is defined according to the following:

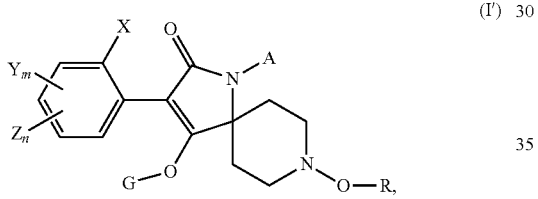

wherein
X, Y and Z independently of each other are $C_{1-4}$alkyl, $C_{3-6}$cycloalkyl, $C_{1-4}$haloalkyl, $C_{1-4}$alkoxy, halogen, phenyl or phenyl substituted by $C_{1-4}$alkyl, $C_{1-4}$haloalkyl, halogen or cyano;
m and n, independently of each other, are 0, 1, 2 or 3 and m+n is 0, 1, 2 or 3;
G is hydrogen, a metal, ammonium, sulfonium or a latentiating group;
R is hydrogen, $C_{1-6}$alkyl, $C_{1-6}$haloalkyl, $C_{1-6}$cyanoalkyl, benzyl, $C_{1-4}$alkoxy($C_{1-4}$)alkyl, $C_{1-4}$alkoxy($C_{1-4}$)alkoxy($C_{1-4}$)alkyl or a group selected from G; and
A is hydrogen, $C_{1-6}$alkyl, $C_{1-6}$haloalkyl, $C_{3-6}$cycloalkyl, $C_{3-6}$cycloalkyl($C_{1-4}$)alkyl, or $C_{3-6}$cycloalkyl($C_{1-4}$)alkyl where in the cycloalkyl moiety a methylene group is replaced by O,S or $NR_0$, where $R_0$ is $C_{1-6}$alkyl or $C_{1-6}$alkoxy, or A is $C_{2-6}$alkenyl, $C_{2-6}$haloalkenyl, $C_{3-6}$alkynyl, $C_{1-6}$cyanoalkyl, benzyl, $C_{1-4}$alkoxy($C_{1-4}$)alkyl, $C_{1-4}$alkoxy($C_{1-4}$)alkoxy($C_{1-4}$)alkyl, oxetanyl, tetrahydrofuranyl, tetrahydropyranyl, $C_{1-6}$alkylcarbonyl, $C_{1-6}$alkoxycarbonyl, $C_{3-6}$cycloalkylcarbonyl, N-di($C_{1-6}$alkyl)carbamoyl, benzoyl, $C_{1-6}$alkylsulfonyl, phenylsulfonyl, $C_{1-4}$alkylthio($C_{1-4}$)alkyl, $C_{1-4}$alkylsulfinyl($C_{1-4}$)alkyl or $C_{1-4}$alkylsulfonyl($C_{1-4}$)alkyl;
or A is $O-A^1$ where $A^1$ is selected from one of A, as defined above, or furanyl-($C_{1-4}$)alkyl, tetrahydro-thiofuranyl, tetrahydro-thiopyranyl or 1-($C_{1-4}$)alkoxy-piperidin-4-yl or an agrochemically acceptable salt or an N-oxide thereof.

Preference is given to using the compound according to formula (I') for controlling phytoparasitic nematodes, more preferably in perennial crops or in annual crops.

Preference is given to using the compound according to formula (I') for controlling nematodes in perennial crops.

Preference is given to using the compound according to formula (I') for controlling nematodes in annual crops.

In a preferred embodiment, the plants treated are in need of protection from nematodes, in particular phytoparasitic nematodes.

Preference is given to the following compounds of formula (I) or formula (I') for use against nematodes in any of the above embodiments of the invention both for use alone or for use with a prior nematicide treated seed or surrounding plant soil:

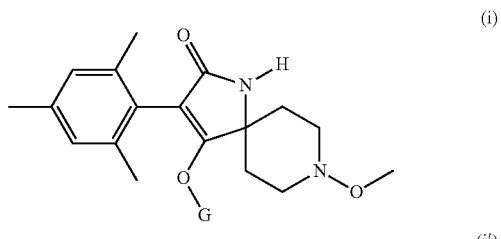
(i)

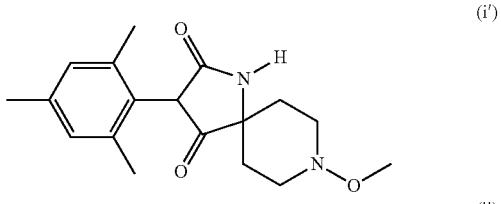
(i')

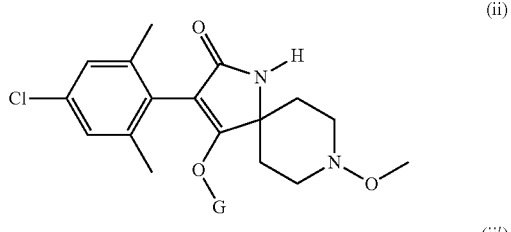
(ii)

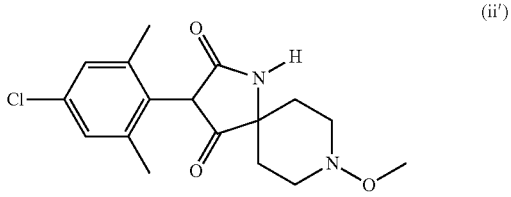
(ii')

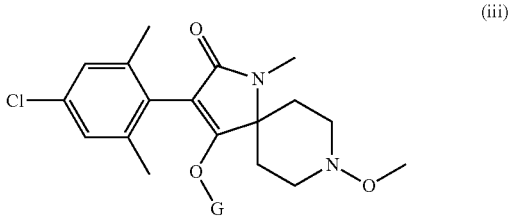
(iii)

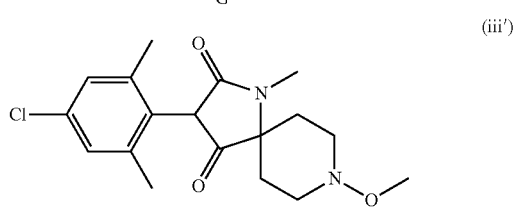
(iii')

-continued (iv)
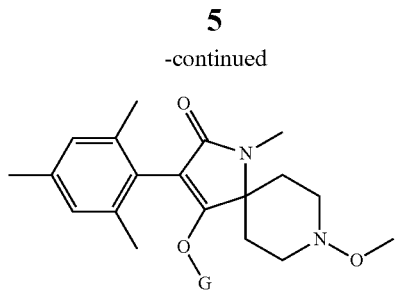

(iv')
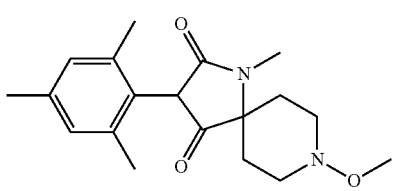

(v)
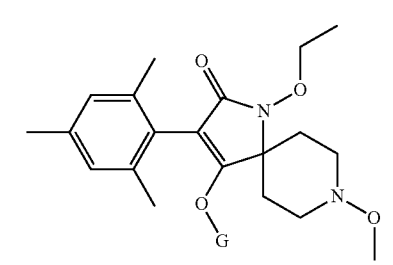

(v')
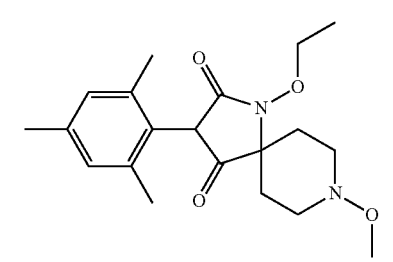

(vi)
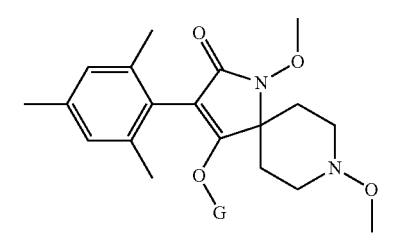

(vi')
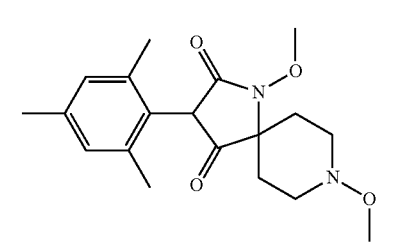

(vii)
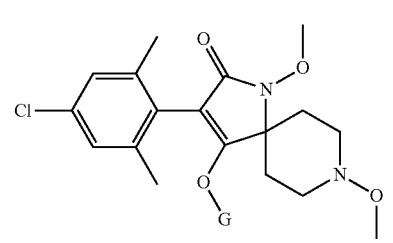

-continued

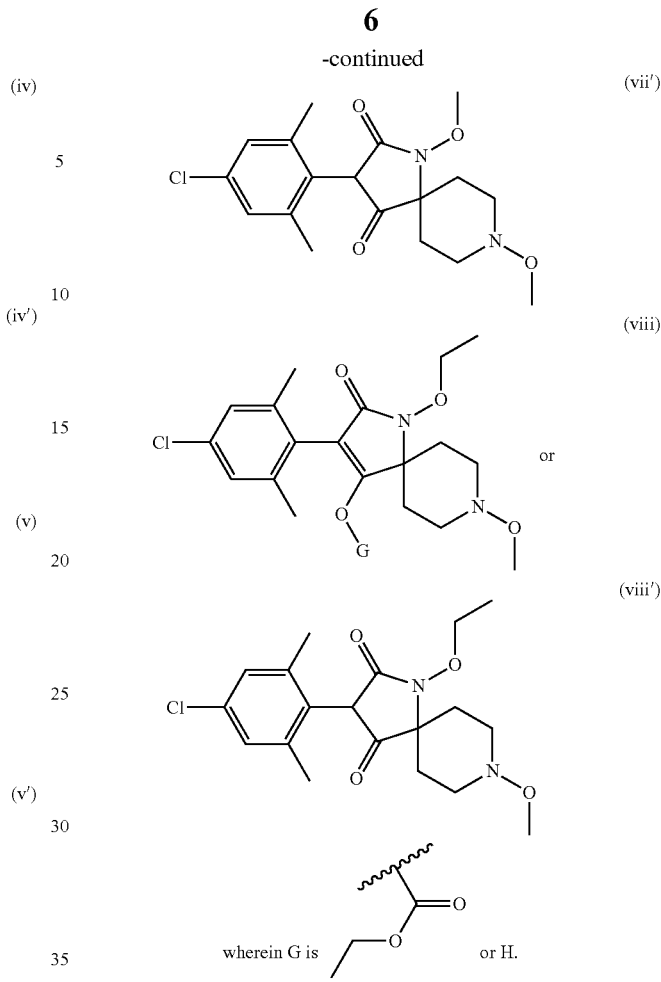

The nematodes targeted in the all of the above-mentioned embodiments are preferably soil-dwelling, phytoparasitic nematodes.

DETAILED DESCRIPTION

Growth-regulating insecticides such as the compounds of the formulae (I) generally act slowly and have no killing effect on adult animals.

Owing to the slow onset of action and a short half-life in the soil, a nematode-controlling application against soil-dwelling nematodes was not expected to be feasable. It is highly surprising that the compounds of the formulae (I) are, after foliar application, suitable for controlling nematodes in spite of the slow onset of action.

Compounds of Formula (I)

In the compounds of formula (I), each alkyl moiety either alone or as part of a larger group is a straight or branched chain and is, for example, methyl, ethyl, n-propyl, n-butyl, iso-propyl, sec-butyl, iso-butyl, and tert-butyl.

Alkoxy groups preferably have a preferred chain length of from 1 to 4 carbon atoms. Alkoxy is, for example, methoxy, ethoxy, propoxy, iso-propoxy, n-butoxy, iso-butoxy, sec-butoxy and tert-butoxy. Such groups can be part of a larger group such as alkoxyalkyl and alkoxyalkoxyalkyl. Alkoxy-alkyl groups preferably have a chain length of 1 to 4 carbon atoms. Alkoxyalkyl is, for example, methoxymethyl, methoxyethyl, ethoxymethyl, ethoxyethyl, n-propoxym-ethyl, n-propoxyethyl or iso-propoxymethyl.

Halogen is generally fluorine, chlorine, bromine or iodine. This also applies, correspondingly, to halogen in combination with other meanings, such as haloalkyl or haloalkoxy.

Haloalkyl and haloalkoxy groups preferably have a chain length of from 1 to 4 carbon atoms. Haloalkyl is, for example, fluoromethyl, difluoromethyl, trifluoromethyl, chloromethyl, dichloromethyl, trichloromethyl, 2,2,2-trifluoroethyl, 2-fluoroethyl, 2-chloroethyl, pentafluoroethyl, 1,1-difluoro-2,2,2-trichloroethyl, 2,2,3,3-tetrafluoroethyl and 2,2,2-trichloroethyl; preferably trichloromethyl, difluorochloromethyl, difluoromethyl, trifluoromethyl and dichlorofluoromethyl. Haloalkoxy is, for example, fluoromethoxy, difluoromethoxy, trifluoromethoxy, chloromethoxy, dichloromethoxy, trichloromethoxy, 2,2,2-trifluoroethoxy, 2-fluoroethoxy, 2-chloroethoxy, pentafluoroethoxy, 1,1-difluoro-2,2,2-trichloroethoxy, 2,2,3,3-tetrafluoroethoxy and 2,2,2-trichloroethoxy; preferably trichloromethoxy, difluorochloromethoxy, difluoromethoxy, trifluoromethoxy and dichlorofluoromethoxy.

The latentiating groups G are selected to allow its removal by one or a combination of biochemical, chemical or physical processes to afford compounds of formula (I) where G is hydrogen before, during or following application to the treated area or plants. Examples of these processes include enzymatic cleavage, chemical hydrolysis and photolysis. Compounds bearing such groups G may offer certain advantages, such as improved penetration of the cuticula of the plants treated, increased tolerance of crops, improved compatibility or stability in formulated mixtures containing other herbicides, herbicide safeners, plant growth regulators, fungicides or insecticides, or reduced leaching in soils.

Such latentiating groups are known in the art, for example, from WO08/071405, WO09/074314, WO09/049851, WO10/063670 and WO10/066780. The latentiating group G is preferably selected from the groups $C_1$-$C_8$alkyl, $C_2$-$C_8$haloalkyl, phenyl$C_1$-$C_8$alkyl (wherein the phenyl may optionally be substituted by $C_1$-$C_3$alkyl, $C_1$-$C_3$haloalkyl, $C_1$-$C_3$alkoxy, $C_1$-$C_3$haloalkoxy, $C_1$-$C_3$alkylthio, $C_1$-$C_3$alkylsulfinyl, $C_1$-$C_3$alkylsulfonyl, halogen, cyano or by nitro), heteroaryl$C_1$-$C_8$alkyl (wherein the heteroaryl may optionally be substituted by $C_1$-$C_3$alkyl, $C_1$-$C_3$haloalkyl, $C_1$-$C_3$alkoxy, $C_1$-$C_3$haloalkoxy, $C_1$-$C_3$alkylthio, $C_1$-$C_3$alkylsulfinyl, $C_1$-$C_3$alkylsulfonyl, halogen, cyano or by nitro), $C_3$-$C_8$alkenyl, $C_3$-$C_8$haloalkenyl, $C_3$-$C_8$alkynyl, $C(X^a)$—$R^a$, $C(X^b)$—$X^c$—$R^b$, $C(X^d)$—$N(R^c)$—$R^d$, —$SO_2$—$R^e$, —$P(X^e)(R^f)$—$R^g$ or $CH_2$—$X^f$—$R^h$ wherein $X^a$, $X^b$, $X^c$, $X^d$, $X^e$ and $X^f$ are independently of each other oxygen or sulfur;

$R^a$ is H, $C_1$-$C_{18}$alkyl, $C_2$-$C_{18}$alkenyl, $C_2$-$C_{18}$alkynyl, $C_1$-$C_{10}$haloalkyl, $C_1$-$C_{10}$cyanoalkyl, $C_1$-$C_{10}$nitroalkyl, $C_1$-$C_{10}$aminoalkyl, $C_1$-$C_5$alkylamino$C_1$-$C_5$alkyl, $C_2$-$C_8$dialkylamino$C_1$-$C_5$alkyl, $C_3$-$C_7$cycloalkyl$C_1$-$C_5$alkyl, $C_1$-$C_5$alkoxy$C_1$-$C_5$alkyl, $C_3$-$C_5$alkenyloxy$C_1$-$C_5$alkyl, $C_3$-$C_5$alkynyl$C_1$-$C_5$oxyalkyl, $C_1$-$C_5$alkylthio$C_1$-$C_5$alkyl, $C_1$-$C_5$alkylsulfinyl$C_1$-$C_5$alkyl, $C_1$-$C_5$alkylsulfonyl$C_1$-$C_5$alkyl, $C_2$-$C_8$alkylideneaminoxy$C_1$-$C_5$alkyl, $C_1$-$C_5$alkylcarbonyl$C_1$-$C_5$alkyl, $C_1$-$C_5$alkoxycarbonyl$C_1$-$C_5$alkyl, aminocarbonyl$C_1$-$C_5$alkyl, $C_1$-$C_5$alkylaminocarbonyl$C_1$-$C_5$alkyl, $C_2$-$C_8$dialkylaminocarbonyl$C_1$-$C_5$alkyl, $C_1$-$C_5$alkylcarbonylamino$C_1$-$C_5$alkyl, N—$C_1$-$C_5$alkylcarbonyl-N—$C_1$-$C_5$alkylamino$C_1$-$C_5$alkyl, $C_3$-$C_6$trialkylsilyl$C_1$-$C_5$alkyl, phenyl$C_1$-$C_5$alkyl (wherein the phenyl may optionally be substituted by $C_1$-$C_3$alkyl, $C_1$-$C_3$haloalkyl, $C_1$-$C_3$alkoxy, $C_1$-$C_3$haloalkoxy, $C_1$-$C_3$alkylthio, $C_1$-$C_3$alkylsulfinyl, $C_1$-$C_3$alkylsulfonyl, halogen, cyano, or by nitro), heteroaryl$C_1$-$C_5$alkyl, (wherein the heteroaryl may optionally be substituted by $C_1$-$C_3$alkyl, $C_1$-$C_3$haloalkyl, $C_1$-$C_3$alkoxy, $C_1$-$C_3$haloalkoxy, $C_1$-$C_3$alkylthio, $C_1$-$C_3$alkylsulfinyl, $C_1$-$C_3$alkylsulfonyl, halogen, cyano, or by nitro), $C_2$-$C_5$haloalkenyl, $C_3$-$C_8$cycloalkyl, phenyl or phenyl substituted by $C_1$-$C_3$alkyl, $C_1$-$C_3$haloalkyl, $C_1$-$C_3$alkoxy, $C_1$-$C_3$haloalkoxy, halogen, cyano or nitro, heteroaryl or heteroaryl substituted by $C_1$-$C_3$ alkyl, $C_1$-$C_3$haloalkyl, $C_1$-$C_3$alkoxy, $C_1$-$C_3$haloalkoxy, halogen, cyano or nitro, $R^b$ is $C_1$-$C_{18}$alkyl, $C_3$-$C_{18}$alkenyl, $C_3$-$C_{18}$alkynyl, $C_2$-$C_{10}$haloalkyl, $C_1$-$C_{10}$cyanoalkyl, $C_1$-$C_{10}$nitroalkyl, $C_2$-$C_{10}$aminoalkyl, $C_1$-$C_5$alkylamino$C_1$-$C_5$alkyl, $C_2$-$C_8$dialkylamino$C_1$-$C_5$alkyl, $C_3$-$C_7$cycloalkyl$C_1$-$C_5$alkyl, $C_1$-$C_5$alkoxy$C_1$-$C_5$alkyl, $C_3$-$C_5$alkenyloxy$C_1$-$C_5$alkyl, $C_3$-$C_5$alkynyloxy$C_1$-$C_5$alkyl, $C_1$-$C_5$alkylthio$C_1$-$C_5$alkyl, $C_1$-$C_5$alkylsulfinyl$C_1$-$C_5$alkyl, $C_1$-$C_5$alkylsulfonyl$C_1$-$C_5$alkyl, $C_2$-$C_8$alkylideneaminoxy$C_1$-$C_5$alkyl, $C_1$-$C_5$alkylcarbonyl$C_1$-$C_5$alkyl, $C_1$-$C_5$alkoxycarbonyl$C_1$-$C_5$alkyl, aminocarbonyl$C_1$-$C_5$alkyl, $C_1$-$C_5$alkylaminocarbonyl$C_1$-$C_5$alkyl, $C_2$-$C_8$dialkylaminocarbonyl$C_1$-$C_5$alkyl, $C_1$-$C_5$alkylcarbonylamino$C_1$-$C_5$alkyl, N—$C_1$-$C_5$alkylcarbonyl-N—$C_1$-$C_5$alkylamino$C_1$-$C_5$alkyl, $C_3$-$C_6$trialkylsilyl$C_1$-$C_5$alkyl, phenyl$C_1$-$C_5$alkyl (wherein the phenyl may optionally be substituted by $C_1$-$C_3$alkyl, $C_1$-$C_3$haloalkyl, $C_1$-$C_3$alkoxy, $C_1$-$C_3$haloalkoxy, $C_1$-$C_3$alkylthio, $C_1$-$C_3$alkylsulfinyl, $C_1$-$C_3$alkylsulfonyl, halogen, cyano, or by nitro), heteroaryl$C_1$-$C_5$alkyl, (wherein the heteroaryl may optionally be substituted by $C_1$-$C_3$alkyl, $C_1$-$C_3$haloalkyl, $C_1$-$C_3$alkoxy, $C_1$-$C_3$haloalkoxy, $C_1$-$C_3$alkylthio, $C_1$-$C_3$alkylsulfinyl, $C_1$-$C_3$alkylsulfonyl, halogen, cyano, or by nitro), $C_3$-$C_5$haloalkenyl, $C_3$-$C_8$cycloalkyl, phenyl or phenyl substituted by $C_1$-$C_3$alkyl, $C_1$-$C_3$haloalkyl, $C_1$-$C_3$alkoxy, $C_1$-$C_3$haloalkoxy, halogen, cyano or nitro, heteroaryl or heteroaryl substituted by $C_1$-$C_3$ alkyl, $C_{1-3}$haloalkyl, $C_1$-$C_3$alkoxy, $C_1$-$C_3$haloalkoxy, halogen, cyano or nitro, $R^c$ and $R^d$ are each independently of each other hydrogen, $C_1$-$C_{10}$alkyl, $C_3$-$C_{10}$alkenyl, $C_3$-$C_{10}$alkynyl, $C_2$-$C_{10}$haloalkyl, $C_1$-$C_{10}$cyanoalkyl, $C_1$-$C_{10}$nitroalkyl, $C_1$-$C_{10}$aminoalkyl, $C_1$-$C_5$alkylamino$C_1$-$C_5$alkyl, $C_2$-$C_8$dialkylamino$C_1$-$C_5$alkyl, $C_3$-$C_7$cycloalkyl$C_1$-$C_5$alkyl, $C_1$-$C_5$alkoxy$C_1$-$C_5$alkyl, $C_3$-$C_5$alkenyloxy$C_1$-$C_5$alkyl, $C_3$-$C_5$alkynyloxy$C_1$-$C_5$alkyl, $C_1$-$C_5$alkylthio$C_1$-$C_5$alkyl, $C_1$-$C_5$alkylsulfinyl$C_1$-$C_5$alkyl, $C_1$-$C_5$alkylsulfonyl$C_1$-$C_5$alkyl, $C_2$-$C_8$alkylideneaminoxy$C_1$-$C_5$alkyl, $C_1$-$C_5$alkylcarbonyl$C_1$-$C_5$alkyl, $C_1$-$C_5$alkoxycarbonyl$C_1$-$C_5$alkyl, aminocarbonyl$C_1$-$C_5$alkyl, $C_1$-$C_5$alkylaminocarbonyl$C_1$-$C_5$alkyl, $C_2$-$C_8$dialkylaminocarbonyl$C_1$-$C_5$alkyl, $C_1$-$C_5$alkylcarbonylamino$C_1$-$C_5$alkyl, N—$C_1$-$C_5$alkylcarbonyl-N—$C_2$-$C_5$alkylaminoalkyl, $C_3$-$C_6$trialkylsilyl$C_1$-$C_5$alkyl, phenyl$C_1$-$C_5$alkyl (wherein the phenyl may optionally be substituted by $C_1$-$C_3$alkyl, $C_1$-$C_3$haloalkyl, $C_1$-$C_3$alkoxy, $C_1$-$C_3$haloalkoxy, $C_1$-$C_3$alkylthio, $C_1$-$C_3$alkylsulfinyl, $C_1$-$C_3$alkylsulfonyl, halogen, cyano, or by nitro), heteroaryl$C_1$-$C_5$alkyl, (wherein the heteroaryl may optionally be substituted by $C_1$-$C_3$alkyl, $C_1$-$C_3$haloalkyl, $C_1$-$C_3$alkoxy, $C_1$-$C_3$haloalkoxy, $C_1$-$C_3$alkylthio, $C_1$-$C_3$alkylsulfinyl, $C_1$-$C_3$alkylsulfonyl, halogen, cyano, or by nitro), $C_2$-$C_5$haloalkenyl, $C_3$-$C_8$cycloalkyl, phenyl or phenyl substituted by $C_1$-$C_3$alkyl, $C_1$-$C_3$haloalkyl, $C_1$-$C_3$alkoxy, $C_1$-$C_3$haloalkoxy, halogen, cyano or nitro, heteroaryl or heteroaryl substituted by $C_1$-$C_3$alkyl, $C_1$-$C_3$haloalkyl, $C_1$-$C_3$alkoxy, $C_1$-$C_3$haloalkoxy, halogen, cyano or nitro, heteroarylamino or heteroarylamino substituted by $C_1$-$C_3$alkyl, $C_1$-$C_3$haloalkyl, $C_1$-$C_3$alkoxy, $C_1$-$C_3$haloalkoxy, halogen, cyano or nitro, diheteroarylamino or diheteroarylamino substituted by $C_1$-$C_3$alkyl, $C_1$-$C_3$haloalkyl, $C_1$-$C_3$alkoxy, $C_1$-$C_3$haloalkoxy, halogen, cyano or nitro, phenylamino or phenylamino substituted by $C_1$-$C_3$alkyl, $C_1$-$C_3$haloalkyl, $C_1$-$C_3$alkoxy, $C_1$-$C_3$haloalkoxy, halogen, cyano or by nitro, diphenylamino or diphenylamino substituted by $C_1$-$C_3$alkyl, $C_1$-$C_3$haloalkyl, $C_1$-$C_3$alkoxy, $C_1$-$C_3$haloalkoxy, halogen, cyano or by nitro or $C_3$-$C_7$cycloalkylamino, di-$C_3$-$C_7$cycloalkylamino or $C_3$-$C_7$cycloalkoxy or $R^c$ and $R^d$ may join together to form a 3-7 membered ring, optionally containing one heteroatom selected from O or S, $R^e$ is $C_1$-$C_{10}$alkyl, $C_2$-$C_{10}$alkenyl, $C_2$-$C_{10}$alkynyl, $C_1$-$C_{10}$haloalkyl, $C_1$-$C_{10}$cyanoalkyl, $C_1$-$C_{10}$nitroalkyl, $C_1$-$C_{10}$aminoalkyl, $C_1$-$C_5$alkylamino$C_1$-$C_5$alkyl, $C_2$-$C_8$dialkylamino$C_1$-$C_5$alkyl, $C_3$-$C_7$cycloalkyl$C_1$-$C_5$alkyl, $C_1$-$C_5$alkoxy$C_1$-$C_5$alkyl, $C_3$-$C_5$alkenyloxy$C_1$-$C_5$alkyl, $C_3$-$C_5$alkynyloxy$C_1$-$C_5$alkyl, $C_1$-$C_5$alkylthio$C_1$-$C_5$alkyl, $C_1$-$C_5$alkylsulfinyl$C_1$-$C_5$alkyl, $C_1$-$C_5$alkylsulfonyl$C_1$-$C_5$alkyl, $C_2$-$C_8$alkylideneaminoxy$C_1$-$C_5$alkyl, $C_1$-$C_5$alkylcarbonyl$C_1$-$C_5$alkyl, $C_1$-$C_5$alkoxycarbonyl$C_1$-$C_5$alkyl, aminocarbonyl$C_1$-$C_5$alkyl, $C_1$-$C_5$alkylaminocarbonyl$C_1$-$C_5$alkyl, $C_2$-$C_8$dialkylaminocarbonyl$C_1$-$C_5$alkyl, $C_1$-$C_5$alkylcarbonylamino$C_1$-$C_5$alkyl, N—$C_1$-$C_5$alkylcarbonyl-N—$C_1$-$C_5$alkylamino$C_1$-$C_5$alkyl, $C_3$-$C_6$trialkylsilyl$C_1$-$C_5$alkyl, phenyl$C_1$-$C_5$alkyl (wherein the phenyl may optionally be substituted by $C_1$-$C_3$alkyl, $C_1$-$C_3$haloalkyl, $C_1$-$C_3$alkoxy, $C_1$-$C_3$haloalkoxy, $C_1$-$C_3$alkylthio, $C_1$-$C_3$alkylsulfinyl, $C_1$-$C_3$alkylsulfonyl, halogen, cyano, or by nitro), heteroaryl$C_1$-$C_5$alkyl (wherein the heteroaryl may optionally be substituted by $C_1$-$C_3$alkyl, $C_1$-$C_3$haloalkyl, $C_1$-$C_3$alkoxy, $C_1$-$C_3$haloalkoxy, $C_1$-$C_3$alkylthio, $C_1$-$C_3$alkylsulfinyl, $C_1$-$C_3$alkylsulfonyl, halogen, cyano, or by nitro), $C_2$-$C_5$haloalkenyl, $C_3$-$C_8$cycloalkyl, phenyl or phenyl substituted by $C_1$-$C_3$alkyl, $C_1$-$C_3$haloalkyl, $C_1$-$C_3$alkoxy, $C_1$-$C_3$haloalkoxy, halogen, cyano or nitro, heteroaryl or heteroaryl substituted by $C_1$-$C_3$ alkyl, $C_1$-$C_3$haloalkyl, $C_1$-$C_3$alkoxy, $C_1$-$C_3$haloalkoxy, halogen, cyano or by nitro, heteroarylamino or heteroarylamino substituted by $C_1$-$C_3$ alkyl, $C_1$-$C_3$haloalkyl, $C_1$-$C_3$alkoxy, $C_1$-$C_3$haloalkoxy, halogen, cyano or by nitro, diheteroarylamino or diheteroarylamino substituted by $C_1$-$C_3$ alkyl, $C_1$-$C_3$haloalkyl, $C_1$-$C_3$alkoxy, $C_1$-$C_3$haloalkoxy, halogen, cyano or nitro, phenylamino or phenylamino substituted by $C_1$-$C_3$alkyl, $C_1$-$C_3$haloalkyl, $C_1$-$C_3$alkoxy, $C_1$-$C_3$haloalkoxy, halogen, cyano or nitro, diphenylamino, or diphenylamino substituted by $C_1$-$C_3$alkyl, $C_1$-$C_3$haloalkyl, $C_1$-$C_3$alkoxy, $C_1$-$C_3$haloalkoxy, halogen, cyano or nitro, or $C_3$-$C_7$cycloalkylamino, di$C_3$-$C_7$cycloalkylamino or $C_3$-$C_7$cycloalkoxy, $C_1$-$C_{10}$alkoxy, $C_1$-$C_{10}$haloalkoxy, $C_1$-$C_5$alkylamino or $C_2$-$C_8$dialkylamino $R^f$ and $R^g$ are each independently of each other $C_1$-$C_{10}$alkyl, $C_2$-$C_{10}$alkenyl, $C_2$-$C_{10}$alkynyl, $C_1$-$C_{10}$alkoxy, $C_1$-$C_{10}$haloalkyl, $C_1$-$C_{10}$cyanoalkyl, $C_1$-$C_{10}$nitroalkyl, $C_1$-$C_{10}$aminoalkyl, $C_1$-$C_5$alkylamino$C_1$-$C_5$alkyl, $C_2$-$C_8$dialkylamino$C_1$-$C_5$alkyl, $C_3$-$C_7$cycloalkyl$C_1$-$C_5$alkyl, $C_1$-$C_5$alkoxy$C_1$-$C_5$alkyl, $C_3$-$C_5$alkenyloxy$C_1$-$C_5$alkyl, $C_3$-$C_5$alkynyloxy$C_1$-$C_5$alkyl, $C_1$-$C_5$alkylthio$C_1$-$C_5$alkyl, $C_1$-$C_5$alkylsulfinyl$C_1$-$C_5$alkyl, $C_1$-$C_5$alkylsulfonyl$C_1$-$C_5$alkyl, $C_2$-$C_8$alkylideneaminoxy$C_1$-$C_5$alkyl, $C_1$-$C_5$alkylcarbonyl$C_1$-$C_5$alkyl, $C_1$-$C_5$alkoxycarbonyl$C_1$-$C_5$alkyl, aminocarbonyl$C_1$-$C_5$alkyl, $C_1$-$C_5$alkylaminocarbonyl$C_1$-$C_5$alkyl, $C_2$-$C_8$dialkylaminocarbonyl$C_1$-$C_5$alkyl, $C_1$-$C_5$alkylcarbonylamino$C_1$-$C_5$alkyl, N—$C_1$-$C_5$alkylcarbonyl-N—$C_2$-$C_5$alkylaminoalkyl, $C_3$-$C_6$trialkylsilyl$C_1$-$C_5$alkyl, phenyl$C_1$-$C_5$alkyl (wherein the phenyl may optionally be substituted by $C_1$-$C_3$alkyl, $C_1$-$C_3$haloalkyl, $C_1$-$C_3$alkoxy, $C_1$-$C_3$haloalkoxy, $C_1$-$C_3$alkylthio, $C_1$-$C_3$alkylsulfinyl, $C_1$-$C_3$alkylsulfonyl, halogen, cyano, or by nitro), heteroaryl$C_1$-$C_5$alkyl (wherein the heteroaryl may optionally be substituted by $C_1$-$C_3$alkyl, $C_1$-$C_3$haloalkyl, $C_1$-$C_3$alkoxy, $C_1$-$C_3$haloalkoxy, $C_1$-$C_3$alkylthio, $C_1$-$C_3$alkylsulfinyl, $C_1$-$C_3$alkylsulfonyl, halogen, cyano, or by nitro), $C_2$-$C_5$haloalkenyl, $C_3$-$C_8$cycloalkyl, phenyl or phenyl substituted by $C_1$-$C_3$alkyl, $C_1$-$C_3$haloalkyl, $C_1$-$C_3$alkoxy, $C_1$-$C_3$haloalkoxy, halogen, cyano or nitro, heteroaryl or heteroaryl substituted by $C_1$-$C_3$ alkyl, $C_1$-$C_3$haloalkyl, $C_1$-$C_3$alkoxy, $C_1$-$C_3$haloalkoxy, halogen, cyano or by nitro, heteroarylamino or heteroarylamino substituted by $C_1$-$C_3$ alkyl, $C_1$-$C_3$haloalkyl, $C_1$-$C_3$alkoxy, $C_1$-$C_3$haloalkoxy, halogen, cyano or by nitro, diheteroarylamino or diheteroarylamino substituted by $C_1$-$C_3$ alkyl, $C_1$-$C_3$haloalkyl, $C_1$-$C_3$alkoxy, $C_1$-$C_3$haloalkoxy, halogen, cyano or nitro, phenylamino or phenylamino substituted by $C_1$-$C_3$alkyl, $C_1$-$C_3$haloalkyl, $C_1$-$C_3$alkoxy, $C_1$-$C_3$haloalkoxy, halogen, cyano or nitro, diphenylamino, or diphenylamino substituted by $C_1$-$C_3$alkyl, $C_1$-$C_3$haloalkyl, $C_1$-$C_3$alkoxy, $C_1$-$C_3$haloalkoxy, halogen, cyano or nitro, or $C_3$-$C_7$cycloalkylamino, di$C_3$-$C_7$cycloalkylamino or $C_3$-$C_7$cycloalkoxy, $C_1$-$C_{10}$haloalkoxy, $C_1$-$C_5$alkylamino or $C_2$-$C_8$dialkylamino, benzyloxy or phenoxy, wherein the benzyl and phenyl groups may in turn be substituted by $C_1$-$C_3$alkyl, $C_1$-$C_3$haloalkyl, $C_1$-$C_3$alkoxy, $C_1$-$C_3$haloalkoxy, halogen, cyano or nitro, and $R^h$ is $C_1$-$C_{10}$alkyl, $C_3$-$C_{10}$alkenyl, $C_3$-$C_{10}$alkynyl, $C_1$-$C_{10}$haloalkyl, $C_1$-$C_{10}$cyanoalkyl, $C_1$-$C_{10}$nitroalkyl, $C_2$-$C_{10}$aminoalkyl, $C_1$-$C_5$alkylamino$C_1$-$C_5$alkyl, $C_2$-$C_8$dialkylamino$C_1$-$C_5$alkyl, $C_3$-$C_7$cycloalkyl$C_1$-$C_5$alkyl, $C_1$-$C_5$alkoxy$C_1$-$C_5$alkyl, $C_3$-$C_5$alkenyloxy$C_1$-$C_5$alkyl, $C_3$-$C_5$alkynyloxy$C_1$-$C_5$alkyl, $C_1$-$C_5$alkylthio$C_1$-$C_5$alkyl, $C_1$-$C_5$alkylsulfinyl$C_1$-$C_5$alkyl, $C_1$-$C_5$alkylsulfonyl$C_1$-$C_5$alkyl, $C_2$-$C_8$alkylideneaminoxy$C_1$-$C_5$alkyl, $C_1$-$C_5$alkylcarbonyl$C_1$-$C_5$alkyl, $C_1$-$C_5$alkoxycarbonyl$C_1$-$C_5$alkyl, aminocarbonyl$C_1$-$C_5$alkyl, $C_1$-$C_5$alkylaminocarbonyl$C_1$-$C_5$alkyl, $C_2$-$C_8$dialkylaminocarbonyl$C_1$-$C_5$alkyl, $C_1$-$C_5$alkylcarbonylamino$C_1$-$C_5$alkyl, N—$C_1$-$C_5$alkylcarbonyl-N—$C_1$-$C_5$alkylamino$C_1$-$C_5$alkyl, $C_3$-$C_6$trialkylsilyl$C_1$-$C_5$alkyl, phenyl$C_1$-$C_5$alkyl (wherein the phenyl may optionally be substituted by $C_1$-$C_3$alkyl, $C_1$-$C_3$haloalkyl, $C_1$-$C_3$alkoxy, $C_1$-$C_3$haloalkoxy, $C_1$-$C_3$alkylthio, $C_1$-$C_3$alkylsulfinyl, $C_1$-$C_3$ alkylsulfonyl, halogen, cyano or by nitro), heteroaryl$C_1$-$C_5$alkyl (wherein the heteroaryl may optionally be substituted by $C_1$-$C_3$alkyl, $C_1$-$C_3$haloalkyl, $C_1$-$C_3$alkoxy, $C_1$-$C_3$haloalkoxy, $C_1$-$C_3$alkylthio, $C_1$-$C_3$alkylsulfinyl, $C_1$-$C_3$ alkylsulfonyl, halogen, cyano or by nitro), phenoxy$C_1$-$C_5$alkyl (wherein the phenyl may optionally be substituted by $C_1$-$C_3$alkyl, $C_1$-$C_3$haloalkyl, $C_1$-$C_3$alkoxy, $C_1$-$C_3$haloalkoxy, $C_1$-$C_3$alkylthio, $C_1$-$C_3$alkylsulfinyl, $C_1$-$C_3$ alkylsulfonyl, halogen, cyano or by nitro), heteroaryloxyC$_1$-C$_5$alkyl (wherein the heteroaryl may optionally be substituted by C$_1$-C$_3$alkyl, C$_1$-C$_3$haloalkyl, C$_1$-C$_3$alkoxy, C$_1$-C$_3$haloalkoxy, C$_1$-C$_3$alkylthio, C$_1$-C$_3$akylsulfinyl, C$_1$-C$_3$ alkylsulfonyl, halogen, cyano or by nitro), C$_3$-C$_5$haloalkenyl, C$_3$-C$_8$cycloalkyl, phenyl or phenyl substituted by C$_1$-C$_3$alkyl, C$_1$-C$_3$haloalkyl, C$_1$-C$_3$alkoxy, C$_1$-C$_3$haloalkoxy, halogen or by nitro, or heteroaryl, or heteroaryl substituted by C$_1$-C$_3$alkyl, C$_1$-C$_3$haloalkyl, C$_1$-C$_3$alkoxy, C$_1$-C$_3$haloalkoxy, halogen, cyano or by nitro.

In particular, the latentiating group G is a group —C(X$^a$)—R$^a$ or —C(X$^b$)—X$^c$—R$^b$, and the meanings of X$^a$, R$^a$, X$^b$, X$^c$ and R$^b$ are as defined above.

In one embodiment, the latentiating group G is selected from the group —C(=O)—R$^a$ and —C(=O)—O—R$^b$; wherein R$^a$ is selected from hydrogen, C$_1$-C$_{12}$alkyl, C$_2$-C$_{12}$alkenyl, C$_2$-C$_{12}$alkynyl, C$_1$-C$_{10}$haloalkyl and R$^b$ is selected from C$_1$-C$_{12}$alkyl, C$_2$-C$_{12}$alkenyl, C$_2$-C$_{12}$alkynyl and C$_1$-C$_{10}$haloalkyl. In particular, R$^a$ and R$^b$ are selected from the group consisting of methyl, ethyl, n-propyl, iso-propyl, n-butyl, iso-butyl, sec-butyl, tert-butyl, ethenyl and propenyl, e.g. 2-propen-1-yl.

It is preferred that G is hydrogen, a metal, preferably an alkali metal or alkaline earth metal, or an ammonium or sulfonium group, where hydrogen is especially preferred.

Depending on the nature of the substituents, compounds of formula (I) may exist in different isomeric forms. When G is hydrogen, for example, compounds of formula (I) may exist in different tautomeric forms:

ine, diethylamine, di-n-propylamine, di-i-propylamine, di-n-butylamine, di-n-amylamine, di-i-amylamine, dihexylamine, diheptylamine, dioctylamine, ethanolamine, n-propanolamine, i-propanolamine, N,N-diethanolamine, N-ethylpropanolamine, N-butylethanolamine, allylamine, n-but-2-enylamine, n-pent-2-enylamine, 2,3-dimethylbut-2-enylamine, dibut-2-enylamine, n-hex-2-enylamine, propylenediamine, trimethylamine, triethylamine, tri-n-propylamine, tri-i-opropylamine, tri-n-butylamine, tri-i-butylamine, tri-sec-butylamine, tri-n-amylamine, methoxyethylamine and ethoxyethylamine; heterocyclic amines, for example pyridine, quinoline, isoquinoline, morpholine, piperidine, pyrrolidine, indoline, quinuclidine and azepine; primary arylamines, for example anilines, methoxyanilines, ethoxyanilines, o-, m- and p-toluidines, phenylenediamines, benzidines, naphthylamines and o-, m- and p-chloroanilines; but especially triethylamine, i-propylamine and di-i-propylamine.

Preferred quaternary ammonium bases suitable for salt formation correspond, for example, to the formula [N(R$_a$ R$_b$ R$_c$ R$_d$)]OH, wherein R$_a$, R$_b$, R$_c$ and R$_d$ are each independently of the others hydrogen or C$_1$-C$_4$alkyl. Further suitable tetraalkylammonium bases with other anions can be obtained, for example, by anion exchange reactions.

Preferred tertiary sulfonium bases suitable for salt formation correspond, for example, to the formula [SR$_e$R$_f$R$_g$]OH, wherein R$_e$, R$_f$ and R$_g$ are each independently of the others C$_1$-C$_4$ alkyl. Trimethylsulfonium hydroxide is especially preferred. Suitable sulfonium bases may be obtained from

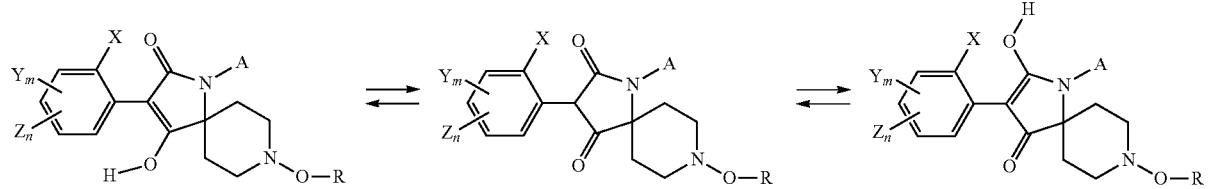

This invention covers all isomers and tautomers and mixtures thereof in all proportions. Also, when substituents contain double bonds, cis- and trans-isomers can exist. These isomers, too, are within the scope of the claimed compounds of the formula (I).

The invention relates also to the agriculturally acceptable salts which the compounds of formula (I) are able to form with transition metal, alkali metal and alkaline earth metal bases, amines, quaternary ammonium bases or tertiary sulfonium bases.

Among the transition metal, alkali metal and alkaline earth metal salt formers, special mention should be made of the hydroxides of copper, iron, lithium, sodium, potassium, magnesium and calcium, and preferably the hydroxides, bicarbonates and carbonates of sodium and potassium.

Examples of amines suitable for ammonium salt formation include ammonia as well as primary, secondary and tertiary C$_1$-C$_{18}$alkylamines, C$_1$-C$_4$hydroxyalkylamines and C$_2$-C$_4$alkoxyalkyl-amines, for example methylamine, ethylamine, n-propylamine, i-propylamine, the four butylamine isomers, n-amylamine, i-amylamine, hexylamine, heptylamine, octylamine, nonylamine, decylamine, pentadecylamine, hexadecylamine, heptadecylamine, octadecylamine, methylethylamine, methylisopropylamine, methylhexylamine, methyl-nonylamine, methylpentadecylamine, methyloctadecylamine, ethylbutylamine, ethylheptyl-amine, ethyloctylamine, hexylheptylamine, hexyloctylamine, dimethylamthe reaction of thioethers, in particular dialkylsulfides, with alkylhalides, followed by conversion to a suitable base, for example a hydroxide, by anion exchange reactions.

The compounds of the invention may be made by a variety of methods as described in detail, for example, in WO09/049851, WO10/063670 and WO10/066780.

It should be understood that in those compounds of formula (I), where G is a metal, ammonium or sulfonium as mentioned above and as such represents a cation, the corresponding negative charge is largely delocalised across the O—C=C—C=O unit.

The compounds of formula (I) according to the invention also include hydrates which may be formed during the salt formation.

Preferably, in the compounds of the formula (I), the substituent R is hydrogen, C$_{1-4}$alkyl, C$_{1-4}$haloalkyl, in particular methyl, ethyl, iso-propyl, n-propyl, tert-butyl, sec-butyl, iso-butyl, or n-butyl.

Preferably, X, Y and Z, are selected, independently of one another, from C$_1$-C$_4$alkyl, C$_1$-C$_4$alkoxy or halogen, in particular methyl, ethyl, iso-propyl, n-propyl, methoxy, fluoro, bromo or chloro, when m+n is 1, 2 or 3, in particular, when m+n is 1 or 2.

Alternatively, Y and Z, independently of each other, denote C$_1$-C$_4$alkyl, C$_1$-C$_4$alkoxy, halogen, in particular methyl, ethyl, iso-propyl, n-propyl, methoxy, fluoro, chloro, bromo, when m+n is 1, 2 or 3, in particular, when m+n is 1 or 2.

In a particular embodiment, in the compound of formula (I), when m is 1, Y is in an ortho position and X and Y are each selected independently from the group consisting of methyl, ethyl, iso-propyl and n-propyl.

In another embodiment, preferably combined with the previous embodiment, wherein when n is 1 in the compound of formula (I), Z is in the para position and is selected from the group consisting of fluoro, bromo and chloro, methyl, ethyl, iso-propyl and n-propyl. Preferably, Z is methyl, fluoro, bromo and chloro. More preferably, Z is chloro or methyl.

In another embodiment, wherein in the compound of formula (I), m and n are each 1, Y is in an ortho position and X and Y are selected independently from the group consisting of methyl and ethyl, and Z is in the para position and is selected from the group consisting of fluoro, bromo and chloro. Preferably, X and Y are each in an ortho position and are methyl and preferably Z is in a para position and is chloro or methyl.

In the compounds of the formula (I), the substituent A is preferably hydrogen, $C_{1-4}$alkyl, $C_{1-4}$haloalkyl, $C_{2-4}$alkenyl, $C_{1-4}$alkoxy($C_{1-4}$)alkyl, $C_{1-4}$alkoxy($C_{1-4}$)alkoxy($C_{1-4}$)alkyl, tetrahydrofuranyl, tetrahydropyranyl, in particular methyl, ethyl, n-propyl, iso-propyl, n-butyl, iso-butyl, sec-butyl, and tert-butyl, trifluoromethyl, 2,2,2-trifluoroethyl, 2,2-difluoroethyl, 2-fluoroethyl, allyl, methoxymethyl, ethoxymethyl, methoxyethyl, methoxypropyl, methoxyethoxymethyl, methoxymethoxyethyl, tetrahydrofuran-2-yl, tetrahydropyran-2-yl, tetrahydrofuran-3-yl, tetrahydropyran-4-yl.

In one embodiment, A is preferably hydrogen.

In another embodiment, A is preferably $C_{1-4}$alkyl. In a preferred embodiment, A is selected from the group consisting of methyl, ethyl, n-propyl, iso-propyl, n-butyl, iso-butyl, sec-butyl, tert-butyl, methoxymethyl, ethoxymethyl and methoxyethyl.

In yet another embodiment, A is preferably selected from the group O-$A^1$, wherein $A^1$ is selected from the group consisting of hydrogen, methyl, ethyl, n-propyl, iso-propyl, n-butyl, iso-butyl, tert-butyl, methoxymethyl, ethoxymethyl, methoxyethyl, methoxypropyl, tetrahydrofuran-2-yl, tetrahydropyran-2-yl, tetrahydrofuran-3-yl and tetrahydropyran-4-yl. Preferably, when A is O-$A^1$, $A^1$ is hydrogen, methyl, ethyl, methoxymethyl, and tetrahydrofuran-2-yl. Even more preferably, when A is O-$A^1$, $A^1$ is methyl or ethyl. Most preferably, when A is O-$A^1$, $A^1$ is methyl.

In another preferred group of compounds of the formula (I), R is one of hydrogen, methyl, ethyl or trifluoroethyl, trifluoromethyl, X is methyl, ethyl or methoxy, Y and Z, independently of each other, are methyl, ethyl, methoxy, fluoro, chloro or bromo, G is hydrogen or a latentiating group selected from the group —C(=O)—$R^a$ and —C(=O)—O—$R^a$; wherein $R^a$ is selected from hydrogen, $C_1$-$C_{12}$alkyl, $C_2$-$C_{12}$alkenyl, $C_2$-$C_{12}$alkynyl, $C_1$-$C_{10}$haloalkyl, and A has the meanings assigned to it above.

In a more preferred group of compounds of the formula (I), R is one of hydrogen, methyl, ethyl, trifluoroethyl, or trifluoromethyl, X is methyl, ethyl or methoxy, Y and Z, independently of each other, are methyl, ethyl, methoxy, fluoro, chloro or bromo, G is hydrogen or a latentiating group selected from the group —C(=O)—$R^a$ and —C(=O)—O—$R^a$; wherein $R^a$ is selected from the group consisting of methyl, ethyl, n-propyl, iso-propyl, n-butyl, iso-butyl, sec-butyl, tert-butyl, ethenyl and propenyl, e.g. 2-propen-1-yl; and A has the meanings assigned to it above.

In a more preferred group of compounds of the formula (I), R is one of hydrogen, methyl, ethyl, trifluoroethyl, or trifluoromethyl, X is methyl, ethyl or methoxy, Y and Z, independently of each other, are methyl, ethyl, methoxy, fluoro, chloro or bromo, G is hydrogen —(C=O)OCH$_2$CH$_3$ and A has the meanings assigned to it above.

In a particularly preferred group of compounds of the formula (I), R is methyl or ethyl, X is methyl, ethyl, methoxy, fluoro, bromo or chloro, Y and Z, independently of each other, are methyl, ethyl, methoxy, fluoro, chloro, or bromo, G is hydrogen or a latentiating group selected from the group —C(=O)—$R^a$ and —C(=O)—O—$R^a$; wherein $R^a$ is selected from hydrogen, $C_1$-$C_{12}$alkyl, $C_2$-$C_{12}$alkenyl, $C_2$-$C_{12}$alkynyl, $C_1$-$C_{10}$haloalkyl, and A has the meanings assigned to it above.

In a particularly preferred group of compounds of the formula (I), R is methyl or ethyl, X is methyl, ethyl, methoxy, fluoro, bromo or chloro, Y and Z, independently of each other, are methyl, ethyl, methoxy, fluoro, chloro, or bromo, G is hydrogen or a latentiating group selected from the group —C(=O)—$R^a$ and —C(=O)—O—$R^a$; wherein preferably $R^a$ is selected from the group consisting of methyl, ethyl, n-propyl, iso-propyl, n-butyl, iso-butyl, sec-butyl, tert-butyl, ethenyl and propenyl, e.g. 2-propen-1-yl, and A has the meanings assigned to it above.

In a particularly preferred group of compounds of the formula (I), R is methyl or ethyl, X is methyl, ethyl, methoxy, fluoro, bromo or chloro, Y and Z, independently of each other, are methyl, ethyl, methoxy, fluoro, chloro, or bromo, G is hydrogen —(C=O)OCH$_2$CH$_3$ and A has the meanings assigned to it above.

In a more preferred group of compounds of the formula (I), R is methyl or ethyl, X is methyl, ethyl, methoxy, fluoro, bromo or chloro, Y and Z, independently of each other, are methyl, ethyl, methoxy, fluoro, chloro, bromo, G is hydrogen or —(C=O)OCH$_2$CH$_3$ and A is hydrogen, methyl, ethyl, isopropyl, trifluoromethyl, 2,2,2-trifluoroethyl, 2,2-difluoroethyl, 2-fluoroethyl, tetrahydrofuran-2-ylmethyl, tetrahydropyran-2-ylmethyl, tetrahydrofuran-3-ylmethyl, tetrahydropyran-3-ylmethyl, tetrahydropyran-4-ylmethyl, allyl, methoxymethyl, ethoxymethyl, methoxyethyl, methoxypropyl, methoxyethoxymethyl, methoxymethoxyethyltetrahydrofuran-2-yl, tetrahydropyran-2-yl, tetrahydrofuran-3-yl, or tetrahydropyran-4-yl.

In a another preferred group of compounds of the formula (I), R is methyl or methoxy, Y and Z, independently of each other, are methyl, ethyl, methoxy, chloro or bromo, G is hydrogen, methoxycarbonyl or propenyloxycarbonyl or —(C=O)OCH$_2$CH$_3$, and A is hydrogen, methyl, ethyl, methoxy, ethoxy, methoxymethyl, tetrahydrofuran-2-yl or tetrahydrofuran-3-yl.

In a another preferred group of compounds of the formula (I), R is methyl, X is methyl or methoxy, Y and Z, independently of each other, are methyl, ethyl, methoxy, chloro or bromo, m is 1, n is 1, G is hydrogen, methoxycarbonyl or propenyloxycarbonyl or —(C=O)OCH$_2$CH$_3$, and A is hydrogen, methyl, ethyl, methoxymethyl, tetrahydrofuran-2-yl or tetrahydrofuran-3-yl.

In another preferred group of compounds of the formula (I), A is hydrogen or $C_{1-4}$alkyl or $C_{1-4}$alkoxy, m is 1, n is 1, X is methyl, Y is in the ortho position and is methyl, Z is in the para position and is methyl, G is hydrogen or —(C=O)OCH$_2$CH$_3$, R is methyl.

In a more preferred group of compounds of the formula (I), A is hydrogen, m is 1, n is 1, X is methyl, Y is in the ortho position and is methyl, Z is in the para position and is methyl, G is hydrogen or —(C=O)OCH$_2$CH$_3$, R is methyl.

In a more preferred group of compounds of the formula (I), A is methyl, m is 1, n is 1, X is methyl, Y is in the ortho position and is methyl, Z is in the para position and is methyl, G is hydrogen or —(C=O)OCH₂CH₃, R is methyl.

In a more preferred group of compounds of the formula (I), A is methoxy, m is 1, n is 1, X is methyl, Y is in the ortho position and is methyl, Z is in the para position and is methyl, G is hydrogen or —(C=O)OCH₂CH₃, R is methyl.

In a more preferred group of compounds of the formula (I), A is ethoxy, m is 1, n is 1, X is methyl, Y is in the ortho position and is methyl, Z is in the para position and is methyl, G is hydrogen or —(C=O)OCH₂CH₃, R is methyl.

In another preferred group of compounds of the formula (I), A is hydrogen or C₁₋₄alkyl or C₁₋₄alkoxy, m is 1, n is 1, X is methyl, Y is in the ortho position and is methyl, Z is in the para position and is chloro, G is hydrogen or —(C=O)OCH₂CH₃, R is methyl.

In a more preferred group of compounds of the formula (I), A is hydrogen, m is 1, n is 1, X is methyl, Y is in the ortho position and is methyl, Z is in the para position and is chloro, G is hydrogen or —(C=O)OCH₂CH₃, R is methyl.

In a more preferred group of compounds of the formula (I), A is methyl, m is 1, n is 1, X is methyl, Y is in the ortho position and is methyl, Z is in the para position and is chloro, G is hydrogen or —(C=O)OCH₂CH₃, R is methyl.

In a more preferred group of compounds of the formula (I), A is methoxy, m is 1, n is 1, X is methyl, Y is in the ortho position and is methyl, Z is in the para position and is chloro, G is hydrogen or —(C=O)OCH₂CH₃, R is methyl.

In a more preferred group of compounds of the formula (I), A is ethoxy, m is 1, n is 1, X is methyl, Y is in the ortho position and is methyl, Z is in the para position and is chloro, G is hydrogen or —(C=O)OCH₂CH₃, R is methyl.

Preferably, the compounds of formula (I) are selected from:

(i)
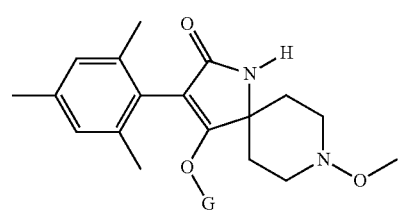

(i')
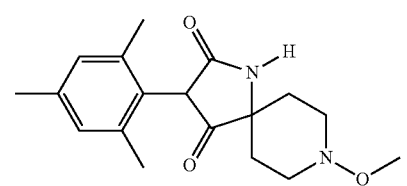

(ii)
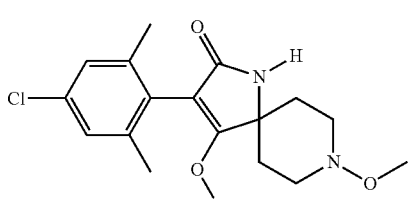

(ii')
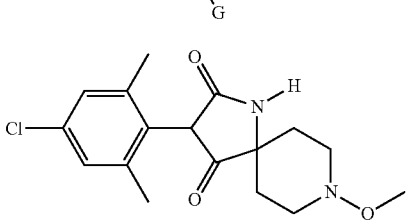

(iii)
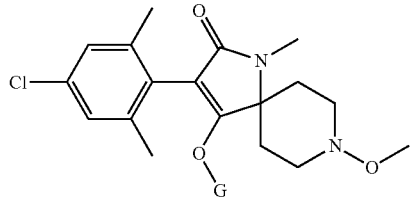

(iii')
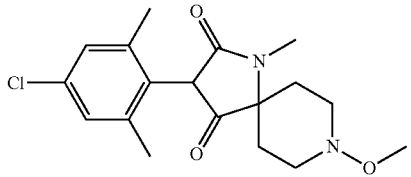

(iv)
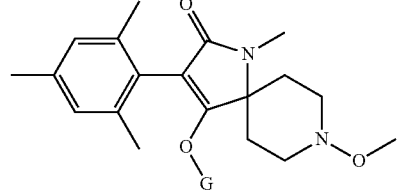

(iv')
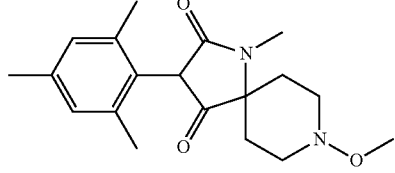

(v)
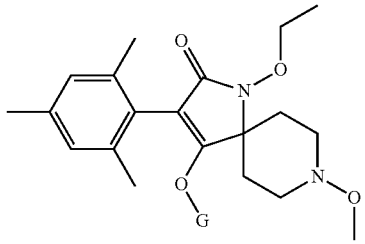

(v')
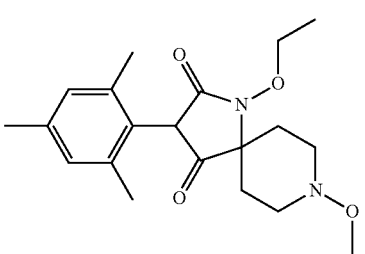

(vi)
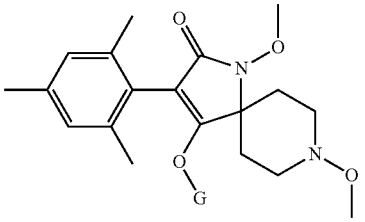

(vi')
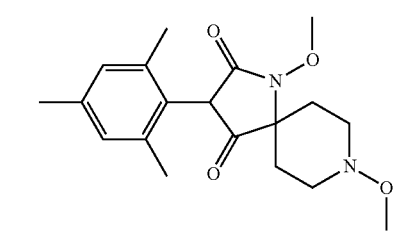
(vii)
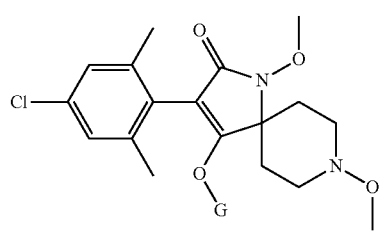
(vii')
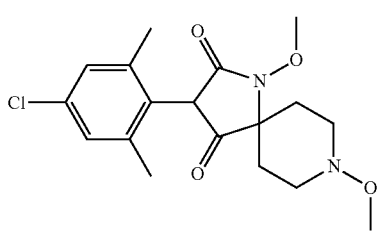
(viii)
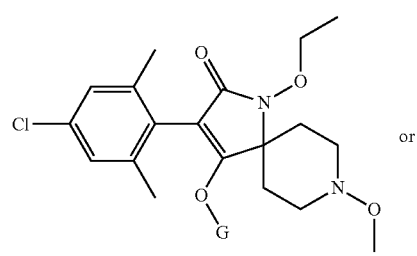
or
(viii')
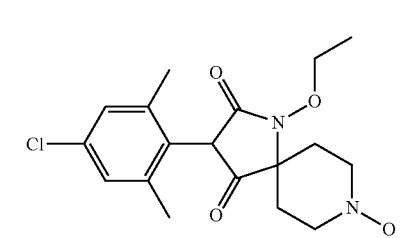
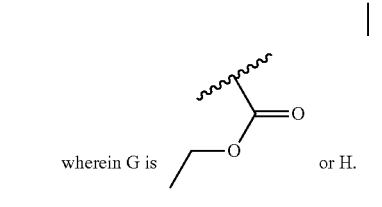
wherein G is ethyl ester group or H.
More preferably, the compounds of formula (I) are selected from:
(i)
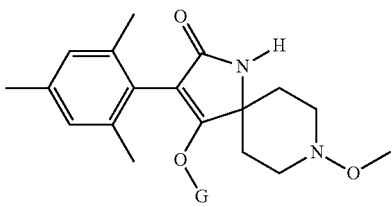
(i')
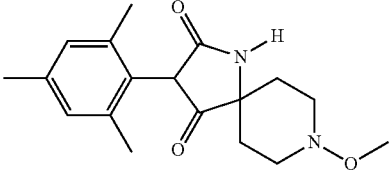
(ii)
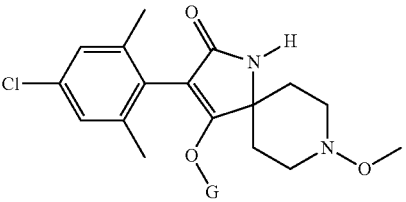
(ii')
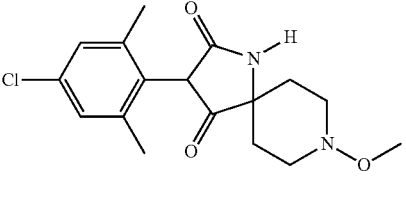
(iii)
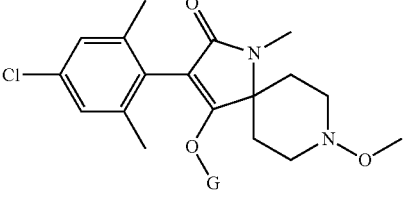
(iii')
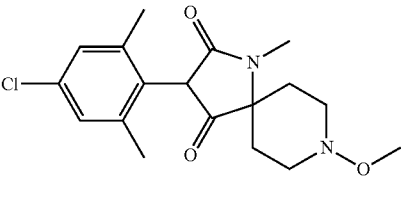
(iv)
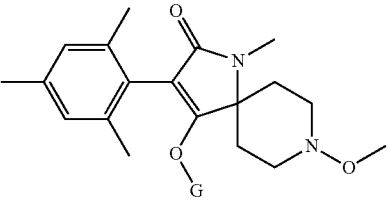
(iv')
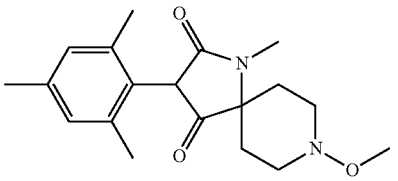

-continued (v) 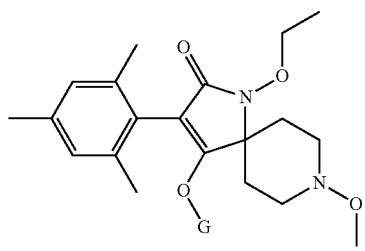

(v') 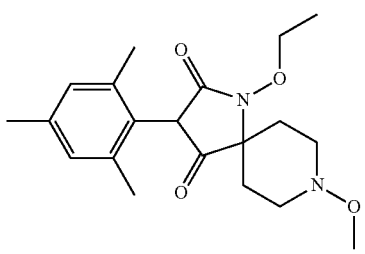

(vi) 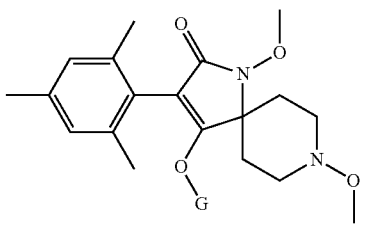

(vi') 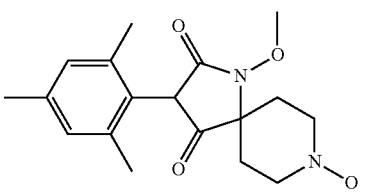

(vii) 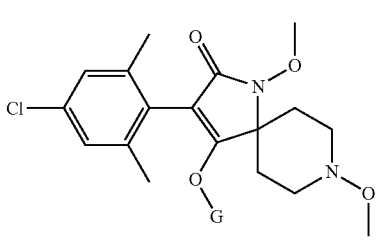

(vii') 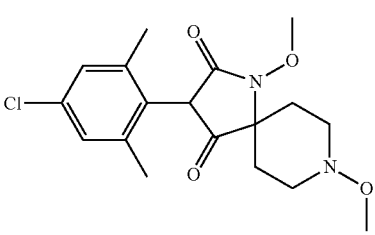

-continued (viii) 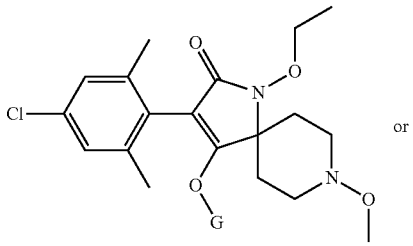 or (viii') 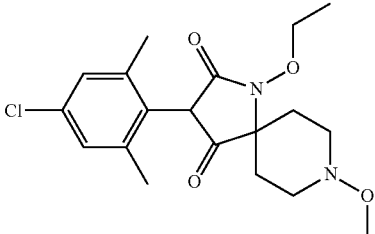

wherein G is 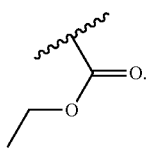

The compositions of the invention may be employed in any conventional form, for example in the form, a powder for dry seed treatment (DS), an emulsion for seed treatment (ES), a flowable concentrate for seed treatment (FS), a solution for seed treatment (LS), a water dispersible powder for seed treatment (WS), a capsule suspension for seed treatment (CF), a gel for seed treatment (GF), an emulsion concentrate (EC), a suspension concentrate (SC), a suspo-emulsion (SE), a capsule suspension (CS), a water dispersible granule (WG), an emulsifiable granule (EG), an emulsion, water in oil (EO), an emulsion, oil in water (EW), a micro-emulsion (ME), an oil dispersion (OD), an oil miscible flowable (OF), an oil miscible liquid (OL), a soluble concentrate (SL), an ultra-low volume suspension (SU), an ultra-low volume liquid (UL), a technical concentrate (TK), a dispersible concentrate (DC), a wettable powder (WP), a soluble granule (SG) or any technically feasible formulation in combination with agriculturally acceptable adjuvants.

Such compositions may be produced in conventional manner, e.g. by mixing the active ingredients with appropriate formulation inerts (diluents, solvents, fillers and optionally other formulating ingredients such as surfactants, biocides, anti-freeze, stickers, thickeners and compounds that provide adjuvancy effects). Also conventional slow release formulations may be employed where long lasting efficacy is intended. Particularly formulations to be applied in spraying forms, such as water dispersible concentrates (e.g. EC, SC, DC, OD, SE, EW, EO and the like), wettable powders and granules, may contain surfactants such as wetting and dispersing agents and other compounds that provide adjuvancy effects, e.g. the condensation product of formaldehyde with naphthalene sulphonate, an alkylarylsulphonate, a lignin sulphonate, a fatty alkyl sulphate, and ethoxylated alkylphenol and an ethoxylated fatty alcohol.

The compositions according to the invention can preferably additionally include an additive comprising an oil of vegetable or animal origin, a mineral oil, alkyl esters of such oils or mixtures of such oils and oil derivatives. The amount of oil additive used in the composition according to the invention is generally from 0.01 to 10%, based on the spray mixture. For example, the oil additive can be added to the spray tank in the desired concentration after the spray mixture has been prepared. Preferred oil additives comprise mineral oils or an oil of vegetable origin, for example rapeseed oil such as ADIGOR® and MERO®, olive oil or sunflower oil, emulsified vegetable oil, such as AMIGO® (Rhône-Poulenc Canada Inc.), alkyl esters of oils of vegetable origin, for example the methyl derivatives, or an oil of animal origin, such as fish oil or beef tallow. A preferred additive contains, for example, as active components essentially 80% by weight alkyl esters of fish oils and 15% by weight methylated rapeseed oil, and also 5% by weight of customary emulsifiers and pH modifiers. Especially preferred oil additives comprise alkyl esters of $C_8$-$C_{22}$ fatty acids, especially the methyl derivatives of $C_{12}$-$C_{18}$ fatty acids, for example the methyl esters of lauric acid, palmitic acid and oleic acid, being important. Those esters are known as methyl laurate (CAS-111-82-0), methyl palmitate (CAS-112-39-0) and methyl oleate (CAS-112-62-9). A preferred fatty acid methyl ester derivative is Emery® 2230 and 2231 (Cognis GmbH). Those and other oil derivatives are also known from the Compendium of Herbicide Adjuvants, 5th Edition, Southern Illinois University, 2000. Also, alkoxylated fatty acids can be used as additives in the inventive compositions as well as polymethylsiloxane based additives, which have been described in WO08/037373.

The application and action of the oil additives can be further improved by combining them with surface-active substances, such as non-ionic, anionic or cationic surfactants. Examples of suitable anionic, non-ionic and cationic surfactants are listed on pages 7 and 8 of WO 97/34485. Preferred surface-active substances are anionic surfactants of the dodecylbenzylsulfonate type, especially the calcium salts thereof, and also non-ionic surfactants of the fatty alcohol ethoxylate type. Special preference is given to ethoxylated $C_{12}$-$C_{22}$ fatty alcohols having a degree of ethoxylation of from 5 to 40. Examples of commercially available surfactants are the Genapol types (Clariant AG). Also preferred are silicone surfactants, especially polyalkyloxide-modified heptamethyltrisiloxanes, which are commercially available e.g. as Silwet L-77®, and also perfluorinated surfactants. The concentration of surface-active substances in relation to the total additive is generally from 1 to 30% by weight. Examples of oil additives that consist of mixtures of oils or mineral oils or derivatives thereof with surfactants are Edenor ME SU®, Turbocharge® (Syngenta AG, CH) and Actipron® (BP Oil UK Limited, GB).

The said surface-active substances may also be used in the formulations alone, that is to say without oil additives.

Furthermore, the addition of an organic solvent to the oil additive/surfactant mixture can contribute to a further enhancement of action. Suitable solvents are, for example, Solvesso® (ESSO) and Aromatic Solvent® (Exxon Corporation). The concentration of such solvents can be from 10 to 80% by weight of the total weight. Such oil additives, which may be in admixture with solvents, are described, for example, in U.S. Pat. No. 4,834,908. A commercially available oil additive disclosed therein is known by the name MERGE® (BASF Corporation). A further oil additive that is preferred according to the invention is SCORE® (Syngenta Crop Protection Canada.)

In addition to the oil additives listed above, in order to enhance the activity of the compositions according to the invention it is also possible for formulations of alkylpyrrolidones, (e.g. Agrimax®) to be added to the spray mixture. Formulations of synthetic latices, such as, for example, polyacrylamide, polyvinyl compounds or poly-1-p-menthene (e.g. Bond®, Courier® or Emerald®) can also be used. Solutions that contain propionic acid, for example Eurogkem Pene-Trate®, can also be mixed into the spray mixture as activity-enhancing agents.

A seed dressing formulation is applied in a manner known per se to the seeds employing the combination of the invention and a diluent in suitable seed dressing formulation form, e.g. as an aqueous suspension or in a dry powder form having good adherence to the seeds. Such seed dressing formulations are known in the art. Seed dressing formulations may contain the single active ingredients or the combination of active ingredients in encapsulated form, e.g. as slow release capsules or microcapsules. A typical a tank-mix formulation for seed treatment application comprises 0.25 to 80%, especially 1 to 75%, of the desired ingredients, and 99.75 to 20%, especially 99 to 25%, of a solid or liquid auxiliaries (including, for example, a solvent such as water), where the auxiliaries can be a surfactant in an amount of 0 to 40%, especially 0.5 to 30%, based on the tank-mix formulation. A typical pre-mix formulation for seed treatment application comprises 0.5 to 99.9%, especially 1 to 95%, of the desired ingredients, and 99.5 to 0.1%, especially 99 to 5%, of a solid or liquid adjuvant (including, for example, a solvent such as water), where the auxiliaries can be a surfactant in an amount of 0 to 50%, especially 0.5 to 40%, based on the pre-mix formulation.

In general, the formulations include from 0.01 to 90% by weight of active agent, from 0 to 20% agriculturally acceptable surfactant and 10 to 99.99% solid or liquid formulation inerts and adjuvant(s), the active agent consisting of at least the compound of formula (I) together with a compound of component B, and optionally other active agents, particularly microbiocides or conservatives or the like. Concentrated forms of compositions generally contain in between about 2 and 80%, preferably between about 5 and 70% by weight of active agent. Application forms of formulation may for example contain from 0.01 to 20% by weight, preferably from 0.01 to 5% by weight of active agent. Whereas commercial products will preferably be formulated as concentrates, the end user will normally employ diluted formulations.

A compound of formula I may be applied by any of the known means of applying pesticidal compounds. For example, it may formulated as an SC, EC, WG, WP, SG, SP, SL, OD, EW diluted and mixed with a tank-mix adjuvant and then applied, to the pests or to a locus of the pests (such as a habitat of the pests, or a growing plant liable to infestation by the pests) or to any part of the plant, including the foliage, stems, branches or roots, directly or it may be sprayed on, applied by dipping, applied as a vapour or applied through distribution or incorporation of a composition (such as a composition packed in a water-soluble bag) in soil or an aqueous environment.

Preferred adjuvants are oil additives e.g. mineral oils or an oil of vegetable origin, for example rapeseed oil such as ADIGOR® and MERO®, olive oil or sunflower oil, emulsified vegetable oil, such as AMIGO® (Rhône-Poulenc Canada Inc.), alkyl esters of oils of vegetable origin, polymeric additives such as Heliosol®, Spodnam® or NuFilm® or Trend90® or polysiloxanes including organosilicones and trisiloxanes e.g. BREAK-THRU® S-240 from Evonik GmbH, BREAK-THRU® S-233 from Evonik GmbH (also known as Complement Super® or Etalfix Pro®), BREAK-THRU® OE441 from Evonik GmbH, BREAK-THRU® OE444 from Evonik GmbH, BREAK-THRU® S243 from Evonik GmbH, BREAK-THRU® OE440 from Evonik GmbH, BREAK-THRU® S200 from Evonik GmbH etc.

The adjuvants can also be a built-in adjuvant.

Preferably, the compounds will be formulated into an SC composition or any other composition to be diluted together with one or more adjuvants selected from the above.

Preferably, the compounds will be applied to the aerial parts of the plants, more preferably only to the aerial parts of the plants. Most preferably, the compounds, for example as a diluted SC composition, will be sprayed onto the aerial parts of the plants.

The crops to be protected, which have only been described in a general manner, are specified in a differentiated and more in-depth manner below.

Targeted Nematodes and Crops

The nematodes which can be targeted according to the invention include but are not limited to, for example, *Pratylenchus* spp., *Radopholus similis*, *Ditylenchus dipsaci*, *Tylenchulus semipenetrans*, *Heterodera* spp., *Globodera* spp., *Meloidogyne* spp., *Aphelenchoides* spp., *Longidorus* spp., *Xiphinema* spp., *Trichodorus* spp., *Bursaphelenchus* spp., *Belonolaimus longicaudatus*, *Mesocriconema xenoplax*, *Tylenchorhynchus* spp., *Rotylenchulus* spp., *Helicotylenchus multicinctus*, *Paratrichodorus* spp., *Paratylenchus* spp., *Criconemella* spp., *Hoplolaimus* spp., *Scutellonema* spp., *Trichostrongylus* spp., *Dolichodorus* spp., *Haemonchus contortus*, *Caenorhabditis elegans* and *Trichostrongylus* spp.

The nematodes which are targeted are preferably soil-dwelling, plant-damaging nematodes i.e. phytoparasitic nematodes: *Pratylenchus* spp., *Radopholus similis*, *Ditylenchus dipsaci*, *Tylenchulus semipenetrans*, *Heterodera* spp., *Globodera* spp., *Meloidogyne* spp., *Aphelenchoides* spp., *Longidorus* spp., *Xiphinema* spp., *Trichodorus* spp., *Bursaphelenchus* spp., *Belonolaimus longicaudatus*, *Mesocriconema xenoplax*, *Tylenchorhynchus* spp., *Rotylenchulus* spp., *Helicotylenchus multicinctus*, *Paratrichodorus* spp., *Paratylenchus* spp., *Criconemella* spp., *Hoplolaimus* spp., *Scutellonema* spp., *Trichostrongylus* spp., *Nacobbus* spp. and *Dolichodorus* spp.

The pyhtoparasitic nematodes most detrimental to crops around the world include *Aphelenchoides* spp. (foliar nematodes), *Ditylenchus dipsaci*, *Globodera* spp. (potato cyst nematodes), *Heterodera* spp (soybean cyst nematodes), *Longidorus* spp., *Meloidogyne* spp. (root-knot nematodes), *Nacobbus* spp., *Pratylenchus* spp. (lesion nematodes), *Trichodorus* spp. and *Xiphinema* spp. (dagger nematodes). Several phytoparasitic nematode species cause histological damages to roots, including the formation of visible galls (e.g. by root-knot nematodes), which are useful characters for their diagnostic in the field. Some nematode species transmit plant viruses through their feeding activity on roots e.g. *Xiphinema index*, vector of grapevine fanleaf virus, an important disease of grapes. Other nematodes attack bark and forest trees. The most important representative of this group is *Bursaphelenchus xylophilus*, the pine wood nematode. *N. aberrans* is an important pest of sugarbeet in North America (Mexico and western USA) and of potatoes in South America.

The nematodes which may be controlled by the invented use of these particular compounds include those nematodes associated with agriculture (which term includes the growing of crops for food and fiber products), horticulture and animal husbandry, companion animals, forestry and the storage of products of vegetable origin (such as fruit, grain and timber); those nematodes associated with the transmission of diseases (e.g. virus transmission).

According to the invention "useful plants" with which the mixture according to the invention can be applied, typically comprise the following species of plants: grape vines; cereals, such as wheat, barley, rye or oats; beet, such as sugar beet or fodder beet; fruits, such as pomes, stone fruits or soft fruits, for example apples, pears, plums, peaches, almonds, cherries, strawberries, raspberries or blackberries; leguminous plants, such as beans, lentils, peas or soybeans; oil plants, such as rape, mustard, poppy, olives, sunflowers, coconut, castor oil plants, cocoa beans or groundnuts; cucumber plants, such as marrows, cucumbers or melons; fibre plants, such as cotton, flax, hemp or jute; citrus fruit, such as oranges, lemons, grapefruit or mandarins; vegetables, such as spinach, lettuce, asparagus, cabbages, carrots, onions, tomatoes, potatoes, cucurbits or paprika; lauraceae, such as avocados, cinnamon or camphor; maize; tobacco; nuts; coffee; sugar cane; tea; vines; hops; durian; bananas; natural rubber plants; turf or ornamentals, such as flowers, shrubs, broad-leaved trees or evergreens, for example conifers. This list does not represent any limitation.

The term "useful plants" is to be understood as including also useful plants that have been rendered tolerant to herbicides like bromoxynil or classes of herbicides (such as, for example, HPPD inhibitors, ACCase inhibitors, ALS inhibitors, for example primisulfuron, prosulfuron and trifloxysulfuron, EPSPS (5-enol-pyrovyl-shikimate-3-phosphate-synthase) inhibitors, GS (glutamine synthetase) inhibitors) as a result of conventional methods of breeding or genetic engineering. An example of a crop that has been rendered tolerant to imidazolinones, e.g. imazamox, by conventional methods of breeding (mutagenesis) is Clearfield® summer rape (Canola). Examples of crops that have been rendered tolerant to herbicides or classes of herbicides by genetic engineering methods include glyphosate- and glufosinate-resistant maize varieties commercially available under the trade names RoundupReady®, Herculex I® and LibertyLink®.

The term "useful plants" is to be understood as including also useful plants which have been so transformed by the use of recombinant DNA techniques that they are capable of synthesising one or more selectively acting toxins, such as are known, for example, from toxin-producing bacteria, especially those of the genus *Bacillus*.

Toxins that can be expressed by such transgenic plants include, for example, insecticidal proteins, for example insecticidal proteins from *Bacillus cereus* or *Bacillus popilliae*; or insecticidal proteins from *Bacillus thuringiensis*, such as δ-endotoxins, e.g. Cry1A(b), Cry1A(c), Cry1F, Cry1F(a2), Cry2A(b), Cry3A, Cry3B(b1) or Cry9c, or vegetative insecticidal proteins (Vip), e.g. Vip1, Vip2, Vip3 or Vip3A; or insecticidal proteins of bacteria colonising nematodes, for example *Photorhabdus* spp. or *Xenorhabdus* spp., such as *Photorhabdus luminescens*, *Xenorhabdus nematophilus*; toxins produced by animals, such as scorpion toxins, arachnid toxins, wasp toxins and other insect-specific neurotoxins; toxins produced by fungi, such as Streptomycetes toxins, plant lectins, such as pea lectins, barley lectins or snowdrop lectins; agglutinins; proteinase inhibitors, such as trypsine inhibitors, serine protease inhibitors, patatin, cystatin, papain inhibitors; ribosome-inactivating proteins (RIP), such as ricin, maize-RIP, abrin, luffin, saporin or bryodin; steroid metabolism enzymes, such as 3-hydroxysteroidoxidase, ecdysteroid-UDP-glycosyl-transferase, cholesterol oxidases, ecdysone inhibitors, HMG-COA-reductase, ion channel blockers, such as blockers of sodium or calcium channels, juvenile hormone esterase, diuretic hormone receptors, stilbene synthase, bibenzyl synthase, chitinases and glucanases.

In the context of the present invention there are to be understood by δ-endotoxins, for example Cry1Ab, Cry1Ac, Cry1F, Cry1Fa2, Cry2Ab, Cry3A, Cry3Bb1 or Cry9C, or vegetative insecticidal proteins (Vip), for example Vip1, Vip2, Vip3 or Vip3A, expressly also hybrid toxins, truncated toxins and modified toxins. Hybrid toxins are produced recombinantly by a new combination of different domains of those proteins (see, for example, WO 02/15701). An example for a truncated toxin is a truncated Cry1A(b), which is expressed in the Bt11 maize from Syngenta Seed SAS, as described below. In the case of modified toxins, one or more amino acids of the naturally occurring toxin are replaced. In such amino acid replacements, preferably non-naturally present protease recognition sequences are inserted into the toxin, such as, for example, in the case of Cry3A055, a cathepsin-G-recognition sequence is inserted into a Cry3A toxin (see WO 03/018810)

Examples of such toxins or transgenic plants capable of synthesising such toxins are disclosed, for example, in EP-A-0 374 753, WO 93/07278, WO 95/34656, EP-A-0 427 529, EP-A-451 878 and WO 03/052073.

The processes for the preparation of such transgenic plants are generally known to the person skilled in the art and are described, for example, in the publications mentioned above. Cry1-type deoxyribonucleic acids and their preparation are known, for example, from WO 95/34656, EP-A-0 367 474, EP-A-0 401 979 and WO 90/13651.

The toxin contained in the transgenic plants imparts to the plants tolerance to harmful insects. Such insects can occur in any taxonomic group of insects, but are especially commonly found in the beetles (Coleoptera), two-winged insects (Diptera) and butterflies (Lepidoptera). Transgenic plants containing one or more genes that code for an insecticidal resistance and express one or more toxins are known and some of them are commercially available. Examples of such plants are: YieldGard® (maize variety that expresses a Cry1A(b) toxin); YieldGard Rootworm® (maize variety that expresses a Cry3B(b1) toxin); YieldGard Plus® (maize variety that expresses a Cry1A(b) and a Cry3B(b1) toxin); Starlink® (maize variety that expresses a Cry9(c) toxin); Herculex I® (maize variety that expresses a Cry1F(a2) toxin and the enzyme phosphinothricine N-acetyltransferase (PAT) to achieve tolerance to the herbicide glufosinate ammonium); NuCOTN 33B® (cotton variety that expresses a Cry1A(c) toxin); Bollgard I® (cotton variety that expresses a Cry1A(c) toxin); Bollgard II® (cotton variety that expresses a Cry1A(c) and a Cry2A(b) toxin); VipCOT® (cotton variety that expresses a Vip3A and a Cry1Ab toxin); NewLeaf® (potato variety that expresses a Cry3A toxin); NatureGard® and Protecta®. Further examples of such transgenic crops are:

1. Bt11 Maize from Syngenta Seeds SAS, Chemin de l'Hobit 27, F-31 790 St. Sauveur, France, registration number C/FR/96/05/10. Genetically modified *Zea mays* which has been rendered resistant to attack by the European corn borer (*Ostrinia nubilalis* and *Sesamia nonagrioides*) by transgenic expression of a truncated Cry1A(b) toxin. Bt11 maize also transgenically expresses the enzyme PAT to achieve tolerance to the herbicide glufosinate ammonium.
2. Bt176 Maize from Syngenta Seeds SAS, Chemin de l'Hobit 27, F-31 790 St. Sauveur, France, registration number C/FR/96/05/10. Genetically modified *Zea mays* which has been rendered resistant to attack by the European corn borer (*Ostrinia nubilalis* and *Sesamia nonagrioides*) by transgenic expression of a Cry1A(b) toxin. Bt176 maize also transgenically expresses the enzyme PAT to achieve tolerance to the herbicide glufosinate ammonium.
3. MIR604 Maize from Syngenta Seeds SAS, Chemin de l'Hobit 27, F-31 790 St. Sauveur, France, registration number C/FR/96/05/10. Maize which has been rendered insect-resistant by transgenic expression of a modified Cry3A toxin. This toxin is Cry3A055 modified by insertion of a cathepsin-G-protease recognition sequence. The preparation of such transgenic maize plants is described in WO 03/018810.
4. MON 863 Maize from Monsanto Europe S.A. 270-272 Avenue de Tervuren, B-1150 Brussels, Belgium, registration number C/DE/02/9. MON 863 expresses a Cry3B (b1) toxin and has resistance to certain Coleoptera insects.
5. IPC 531 Cotton from Monsanto Europe S.A. 270-272 Avenue de Tervuren, B-1150 Brussels, Belgium, registration number C/ES/96/02.
6. 1507 Maize from Pioneer Overseas Corporation, Avenue Tedesco, 7 B-1160 Brussels, Belgium, registration number C/NL/00/10. Genetically modified maize for the expression of the protein Cry1F for achieving resistance to certain Lepidoptera insects and of the PAT protein for achieving tolerance to the herbicide glufosinate ammonium.
7. NK603×MON 810 Maize from Monsanto Europe S.A. 270-272 Avenue de Tervuren, B-1150 Brussels, Belgium, registration number C/GB/02/M3/03. Consists of conventionally bred hybrid maize varieties by crossing the genetically modified varieties NK603 and MON 810. NK603×MON 810 Maize transgenically expresses the protein CP4 EPSPS, obtained from *Agrobacterium* sp. strain CP4, which imparts tolerance to the herbicide Roundup® (contains glyphosate), and also a Cry1A(b) toxin obtained from *Bacillus thuringiensis* subsp. *kurstaki* which brings about tolerance to certain Lepidoptera, include the European corn borer.

Transgenic crops of insect-resistant plants are also described in BATS (Zentrum für Biosicherheit and Nachhaltigkeit, Zentrum BATS, Clarastrasse 13, 4058 Basel, Switzerland) Report 2003, (http://bats.ch).

The term "useful plants" is to be understood as including also useful plants which have been so transformed by the use of recombinant DNA techniques that they are capable of synthesising antipathogenic substances having a selective action, such as, for example, the so-called "pathogenesis-related proteins" (PRPs, see e.g. EP-A-0 392 225). Examples of such antipathogenic substances and transgenic plants capable of synthesising such antipathogenic substances are known, for example, from EP-A-0 392 225, WO 95/33818, and EP-A-0 353 191. The methods of producing such transgenic plants are generally known to the person skilled in the art and are described, for example, in the publications mentioned above.

Antipathogenic substances which can be expressed by such transgenic plants include, for example, ion channel blockers, such as blockers for sodium and calcium channels, for example the viral KP1, KP4 or KP6 toxins; stilbene synthases; bibenzyl synthases; chitinases; glucanases; the so-called "pathogenesis-related proteins" (PRPs; see e.g. EP-A-0 392 225); antipathogenic substances produced by microorganisms, for example peptide antibiotics or heterocyclic antibiotics (see e.g. WO 95/33818) or protein or polypeptide factors involved in plant pathogen defence (so-called "plant disease resistance genes", as described in WO 03/000906). The terms "crop", "crops", "useful plants", "crop plants", "agricultural plants", "food plants" are used interchangeably herein.

Useful plants of elevated interest in connection with present invention are cereals; soybean; rice; oil seed rape; pome fruits; stone fruits; peanuts; coffee; tea; strawberries; turf; vines and vegetables, such as tomatoes, potatoes, cucurbits and lettuce.

Perennial crops are to be understood as meaning citrus fruit, pomme fruit, stone fruit, grapevine, tea, almonds, nuts, coffee, tropical fruit, soft fruit, ornamental plants, lawn and olives.

Annual crops are to be understood as meaning vegetable, tobacco, melons, beet, sugar beet, cereals, corn, cotton, soya and potatoes.

Thus, with a view to application, citrus fruit is to be understood as meaning, for example, oranges, Clementines, satsumas, lemons, grapefruits, cumquats, mandarines, furthermore pomme fruit, such as apples, pears, but also stone fruit, such as peaches, nectarines, cherries, apricots, furthermore grapevine, olives, tea, and tropical crops, such as, for example, mangoes, papayas, figs, pineapples, dates, bananas, durians, passion fruit, kakis, coconuts, cacao, coffee, avocados, lychees, maracujas, guavas, sugar cane, moreover almonds and nuts, such as, for example, hazelnuts, walnuts, pistachios, cashew nuts, brazil nuts, pecan nuts, butter nuts, chestnuts, hickory nuts, macadamia nuts, peanuts, additionally also soft fruit, such as, for example, blackcurrants, gooseberries, raspberries, blackberries, blueberries, strawberries, red bilberries, kiwis, cranberries.

With respect to the use, ornamental plants are to be understood as meaning, for example, cut flowers, such as, for example, roses, carnations, gerbera, lilies, marguerites, chrysanthemums, tulips, daffodils, anemones, poppies, amaryllis, dahlias, azaleas, malves, gardenias, euphorbias, furthermore, for example, bedding plants, potted plants and shrubs, such as, for example, roses, hibiscus, chrysanthemums, furthermore, for example, bushes and conifers, such as, for example, fig trees, rhododendron, spruce trees, fir trees, pine trees, yew trees, juniper trees, but also lawn, such as, for example, golf lawn, garden lawn.

With respect to the use, vegetables are understood as meaning for example fruiting vegetables and inflorescences as vegetables, for example bell peppers, chillies, tomatoes, aubergines, cucumbers, pumpkins, courgettes, broad beans, climbing and dwarf beans, peas, artichokes, maize; but also leafy vegetables, for example head-forming lettuce, chicory, endives, various types of cress, of rocket, lamb's lettuce, iceberg lettuce, leeks, spinach, Swiss chard; furthermore tuber vegetables, root vegetables and stem vegetables, for example celeriac/celery, beetroot, carrots, radish, horseradish, scorzonera, asparagus, beet for human consumption, palm hearts, bamboo shoots, furthermore bulb vegetables, for example onions, leeks, Florence fennel, garlic; furthermore Brassica vegetables such as cauliflower, broccoli, kohlrabi, red cabbage, white cabbage, curly kale, Savoy cabbage, Brussels sprouts, Chinese cabbage.

With respect to the use in cereal crops, cereal is to be understood as meaning, for example, wheat, barley, rye, oats, triticale but also maize and millet.

Particularly preference for the use of the compounds according to the invention are target nematodes from the following families, preferably found in the below-mentioned crops/useful plants:

Pratylenchidae,
Radopholus brevicaudatus, Radopholus cavenessi, Radopholus clarus, Radopholus citrophilus, Radopholus crenatus, Radopholus inaequalis, Radopholus inanis, Radopholus capitatus, Radopholus intermedius, Radopholus laevis, Radopholus litoralis, Radopholus magniglans, Radopholus megadorus, Radopholus nativus, Radopholus neosimilis, Radopholus nigeriensis, Radopholus rectus, Radopholus rotundisemenus, Radopholus serratus, Radopholus similis, Radopholus trilineatus, Radopholus triversus, Radopholus vacuus, Radopholus vangundyi, Radopholus vertexplanus, Radopholus williamsi
  in citrus fruit, tropical fruit e.g. bananas, coffee, coconuts, avocado; tea, ornamental plants, lawn Pratylenchus coffeae, Pratylenchus fallax strawberries, Pratylenchus goodeyi, Pratylenchus vulnus, Pratylenchus penetrans, Pratylenchus brachyurus
  in tropical fruit, e.g. bananas, coffee, pineapples; nuts, e.g. walnuts, almonds; ornamental plants e.g. roses;

Particular preference is furthermore given to
Xiphinema americanum, Xiphinema diversicaudatum, Xiphinema index
  in crops such as grapevines, soft fruit e.g. strawberries; conifers e.g. pines; ornamental plants, e.g. roses; stone fruit Longidorus elongates
  in crops such as soft fruit e.g. strawberries; shrubs, perennial crops Meloidogyne incognita, Meloidogyne hapla, Meloidogyne arenaria, Meloidogyne javanica
  in crops such as grapevines, peanuts, sugar cane, tomatoes Tylenchulus semipenetrans (Family: Tylenchulidae)
  in crops such as citrus fruit e.g. oranges, grapefruits, lemons, mandarins; grapevines, olives, tropical fruit e.g. persimmon;

Belonolaimus longicaudatus (Family: Belonolaimidae)
  in crops such as citrus fruit e.g. oranges, grapefruits, lemons, mandarins; soft fruit e.g. strawberries; lawn, conifers e.g. spruce;

Mesocriconema xenoplax
  in crops such as grapevines, nuts, e.g. almonds, walnuts;

Rotylenchulus reniformis
  in crops such as tropical fruit e.g. bananas, pineapples, papayas, melons, passion fruit; coffee, in citrus fruit e.g. oranges, grapefruits; ornamental plants e.g. gardenias, euphorbias Helicotylenchus multicinctus
  in crops such as tropical fruit e.g. bananas All plants and plant parts can be treated in accordance with the invention. Preferably, the compound according to formula (I) is used to treat the aerial part of the plant (e.g. leaves, needles, stalks, stems, flowers, fruit bodies, fruits).

In this context, plants are understood as meaning all plants and plant populations such as desired and undesired wild plants or crop plants (including naturally occurring crop plants).

Crop plants can be plants which can be obtained by traditional breeding and optimization methods or by biotechnological and recombinant methods, or combinations of these methods, including the transgenic plants and including the plant varieties which are capable or not capable of being protected by Plant Breeders' Rights.

Plant parts are understood as meaning all aerial and subterranean parts and organs of the plants such as shoot, leaf, flower and root, examples which may be mentioned being leaves, needles, stalks, stems, flowers, fruit bodies, fruits and seeds, but also roots, tubers and rhizomes.

The plant parts also include crop material and vegetative and generative propagation material, for example cuttings, tubers, rhizomes, slips and seeds.

The treatment according to the invention with the active compound, of the plants and plant parts, is effected directly or by treating their environment, habitat or store using conventional treatment methods, for example by dipping, spraying, fumigating, fogging, scattering, brushing on, injecting, and, in the case of propagation material, in particular seeds, furthermore by coating with one or more coats.

As already mentioned above, all plants and their parts can be treated in accordance with the invention.

The terms "parts", "parts of plants" or "plant parts" were described above.

One Step Method

In the first embodiment of the invention the method for combating and controlling nematodes in the soil of crops comprises the step of applying a treatment of the compound according to formula (I) as described above to said crops.

Generally, the compound according to formula (I) is applied to the crop plants at a rate of from 1 to 1000 g/ha, preferably 1 to 500 g/ha, more preferably 10 to 400 g/ha, most preferably 30 to 400 g/ha.

In a specific embodiment, the compound according to formula (I) is the only nematicide applied as a treatment to the plant. In this specific embodiment, the compound according to formula (I) is applied to the crop plants at a rate of from 1 to 1000 g/ha, preferably 1 to 500 g/ha, more preferably 10 to 400 g/ha, most preferably 30 to 400 g/ha.

In another embodiment, the compound according to formula (I) is applied with a second chemical nematicide applied to the plant. The second chemical nematicide can be selected from 1,2-dibromo-3-chloropropane, 1,2-dichloropropane, 1,2-dichloropropane with 1,3-dichloropropene, 1,3-dichloropropene, 3,4-dichlorotetrahydrothiophene 1,1-dioxide, 3-(4-chlorophenyl)-5-methylrhodanine, 5-methyl-6-thioxo-1,3,5-thiadiazinan-3-ylacetic acid, 6-isopentenylaminopurine, abamectin, acetoprole, alanycarb, aldicarb, aldoxycarb, benclothiaz, benomyl, butylpyridaben, cadusafos, carbofuran, carbon disulfide, carbosulfan, chloropicrin, chlorpyrifos, cloethocarb, cytokinins, dazomet, DBCP, DCIP, diamidafos, dichlofenthion, dicliphos, dimethoate, doramectin, emamectin, emamectin benzoate, eprinomectin, ethoprophos, ethylene dibromide, fenamiphos, fenpyrad, fensulfothion, fluensulfone, fosthiazate, fosthietan, furfural, GY-81, heterophos, imicyafos, imicyafos, iodomethane, isamidofos, isazofos, ivermectin, kinetin, mecarphon, metam, metam-potassium, metam-sodium, methyl bromide, methyl isothiocyanate, milbemycin oxime, moxidectin, *Myrothecium verrucaria* composition, oxamyl, oxamyl carbamate, phorate, phosphamidon, phosphocarb, sebufos, selamectin, spinosad, terbam, terbufos, tetrachlorothiophene, thiafenox, thionazin, triazophos, triazuron, xylenols, YI-5302 and zeatin. In this specific embodiment, the compound according to formula (I) is applied to the crop plants at a rate of from 1 to 1000 g/ha, preferably 1 to 500 g/ha, more preferably 10 to 400 g/ha and most preferably 30 to 400 g/ha and the second nematicide is applied to the crop plants at a rate of from 1 to 1000 g/ha, preferably 1 to 500 g/ha, more preferably 10 to 400 g/ha and most preferably 30 to 400 g/ha.

In all of the embodiments above the compound according to formula (I) is preferably applied as a foliar treatment to said crop plants.

The compound according to formula (I) is preferably applied on the aerial part of said crop plants. The compound according to formula (I) is preferably sprayed on the aerial part of said crop plants.

In a preferred embodiment, the plants treated are in need of protection from nematodes, in particular phytoparasitic nematodes.

Two Step Method

The invention also covers a method to combat and control nematodes comprising at least two treatments, namely:
  i) applying a first composition with nematicidal properties to a seed and/or to the soil surrounding a planted seed or plant;
  ii) and applying a second composition comprising a systemic nematicidal compound to an aerial plant part of said plant or plant produced from the seed;
wherein the systemic nematicidal compound is selected from a compound according to formula (I')

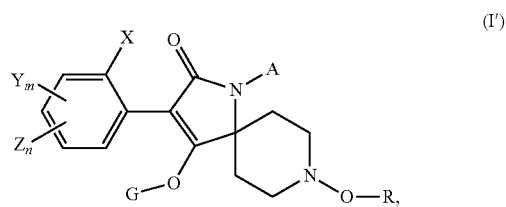

wherein
  X, Y and Z independently of each other are $C_{1-4}$alkyl, $C_{3-6}$cycloalkyl, $C_{1-4}$haloalkyl, $C_{1-4}$alkoxy, halogen, phenyl or phenyl substituted by $C_{1-4}$alkyl, $C_{1-4}$haloalkyl, halogen or cyano;
  m and n, independently of each other, are 0, 1, 2 or 3 and m+n is 0, 1, 2 or 3;
  G is hydrogen, a metal, ammonium, sulfonium or a latentiating group;
  R is hydrogen, $C_{1-6}$alkyl, $C_{1-6}$haloalkyl, $C_{1-6}$cyanoalkyl, benzyl, $C_{1-4}$alkoxy($C_{1-4}$)alkyl, $C_{1-4}$alkoxy($C_{1-4}$)alkoxy($C_{1-4}$)alkyl or a group selected from G; and
  A is hydrogen, $C_{1-6}$alkyl, $C_{1-6}$haloalkyl, $C_{3-6}$cycloalkyl, $C_{3-6}$cycloalkyl($C_{1-4}$)alkyl, or $C_{3-6}$cycloalkyl($C_{1-4}$)alkyl where in the cycloalkyl moiety a methylene group is replaced by O, S or $NR_0$, where $R_0$ is $C_{1-6}$alkyl or $C_{1-6}$alkoxy, or A is $C_{2-6}$alkenyl, $C_{2-6}$haloalkenyl, $C_{3-6}$alkynyl, $C_{1-6}$cyanoalkyl, benzyl, $C_{1-4}$alkoxy($C_{1-4}$)alkyl, $C_{1-4}$alkoxy($C_{1-4}$)alkoxy($C_{1-4}$)alkyl, oxetanyl, tetrahydrofuranyl, tetrahydropyranyl, $C_{1-6}$alkylcarbonyl, $C_{1-6}$alkoxycarbonyl, $C_{3-6}$cycloalkylcarbonyl, N-di($C_{1-6}$alkyl)carbamoyl, benzoyl, $C_{1-6}$alkylsulfonyl, phenylsulfonyl, $C_{1-4}$alkylthio($C_{1-4}$)alkyl, $C_{1-4}$alkylsulfinyl($C_{1-4}$)alkyl or $C_{1-4}$alkylsulfonyl($C_{1-4}$)alkyl;
  or A is $O-A^1$ where $A^1$ is selected from one of A, as defined above, or furanyl-($C_{1-4}$)alkyl, tetrahydro-thiofuranyl, tetrahydro-thiopyranyl or 1-($C_{1-4}$)alkoxy-piperidin-4-yl or an agrochemically acceptable salt or an N-oxide thereof.

The combination of the first composition and the second composition provides synergistic control of the nematodes. By synergistic control, it is herein understood that the effect achieved with the combination of the first composition and the second composition is greater than the expected sum of effects of the first and second compositions taken individually. This can be measured and calculated according to the Colby method explained below.

The action to be expected E for a given active ingredient combination obeys the so-called COLBY formula and can be calculated as follows (COLBY, S. R. "Calculating synergistic and antagonistic responses of herbicide combination". Weeds, Vol. 15, pages 20-22; 1967):

ppm=milligrams of active ingredient (=a.i.) per liter of spray mixture

X=% action by active ingredient A) using p ppm of active ingredient

Y=% action by active ingredient B) using q ppm of active ingredient.

According to COLBY, the expected (additive) action of active ingredients A)+B) using p+q ppm of active ingredient is $$E = X + Y - \frac{X \cdot Y}{100}$$

If the action actually observed (O) is greater than the expected action (E), then the action of the combination is super-additive, i.e. there is a synergistic effect. In mathematical terms the synergism factor SF corresponds to O/E. In the agricultural practice an SF of ≥1.2 indicates significant improvement over the purely complementary addition of activities (expected activity), while an SF of ≤0.9 in the practical application routine signals a loss of activity compared to the expected activity.

Preferably, in this embodiment the compounds of formula (I') are selected from compounds wherein:

X, Y and Z independently of each other are methyl, ethyl, iso-propyl, n-propyl, methoxy, fluoro, bromo or chloro;
m and n, independently of each other, are 0, 1, 2 and m+n is 0, 1, 2;
G is hydrogen, or a latentiating group;
R is hydrogen, methyl, ethyl, iso-propyl, n-propyl, tert-butyl, sec-butyl, iso-butyl, or n-butyl;
A is hydrogen, methyl, ethyl, n-propyl, iso-propyl, methoxy, ethoxy, methoxymethyl, ethoxymethyl, methoxyethyl.

More preferably, in this embodiment the compounds of formula (I') are selected from compounds wherein:

X, Y and Z independently of each other are methyl, ethyl, fluoro, bromo or chloro;
m and n, independently of each other, are 0, 1, 2 and m+n is 1, 2;
G is hydrogen, or a latentiating group;
R is hydrogen, methyl or ethyl; and
A is hydrogen, methyl, ethyl, methoxy, ethoxy.

Most preferably, in this embodiment the compounds of formula (I') are selected from compounds wherein:

X, Y and Z independently of each other are methyl or chloro;
m and n, independently of each other, are 0, 1, 2 and m+n is 1, 2;
G is hydrogen, or a latentiating group;
R is hydrogen, methyl; and
A is hydrogen, methyl, methoxy.

In the above groups of compounds of the formula (I'), G is preferably hydrogen or a latentiating group selected from the group —C(=O)—R$^a$ and —C(=O)—O—R$^a$; wherein R$^a$ is selected from hydrogen, $C_1$-$C_{12}$alkyl, $C_2$-$C_{12}$alkenyl, $C_2$-$C_{12}$alkynyl, $C_1$-$C_{10}$haloalkyl.

In the above groups of compounds of the formula (I'), G is more preferably hydrogen or a latentiating group selected from the group —C(=O)—R$^a$ and —C(=O)—O—R$^a$; wherein R$^a$ is selected from the group consisting of methyl, ethyl, n-propyl, iso-propyl, n-butyl, iso-butyl, sec-butyl, tert-butyl, ethenyl and propenyl, e.g. 2-propen-1-yl.

In the above groups of compounds of the formula (I'), G is more preferably hydrogen or —(C=O)OCH$_2$CH$_3$.

Preferably, the compounds of formula (I') are selected from:

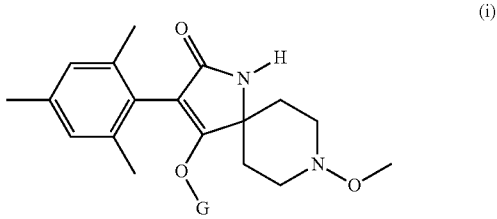

(i)

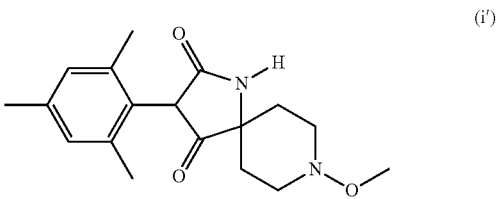

(i')

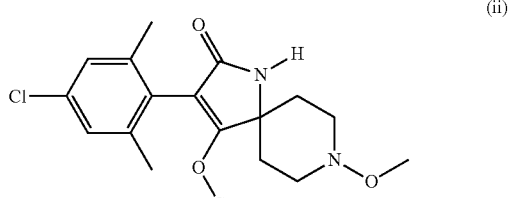

(ii)

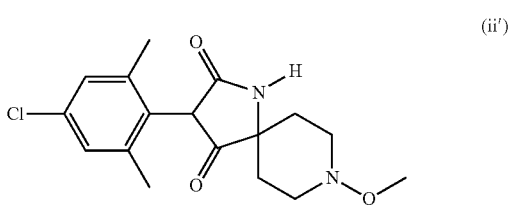

(ii')

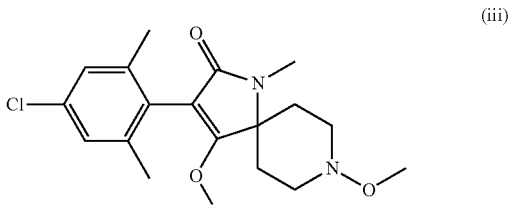

(iii)

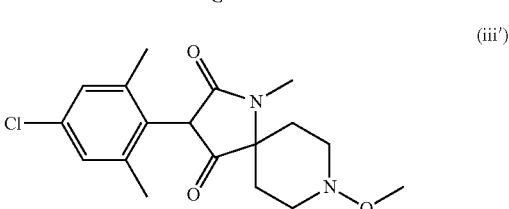

(iii')

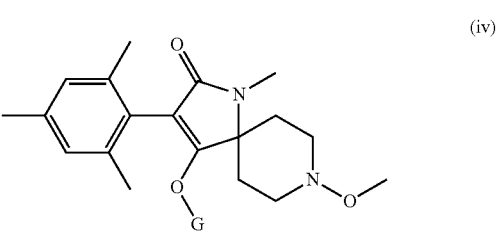

(iv)

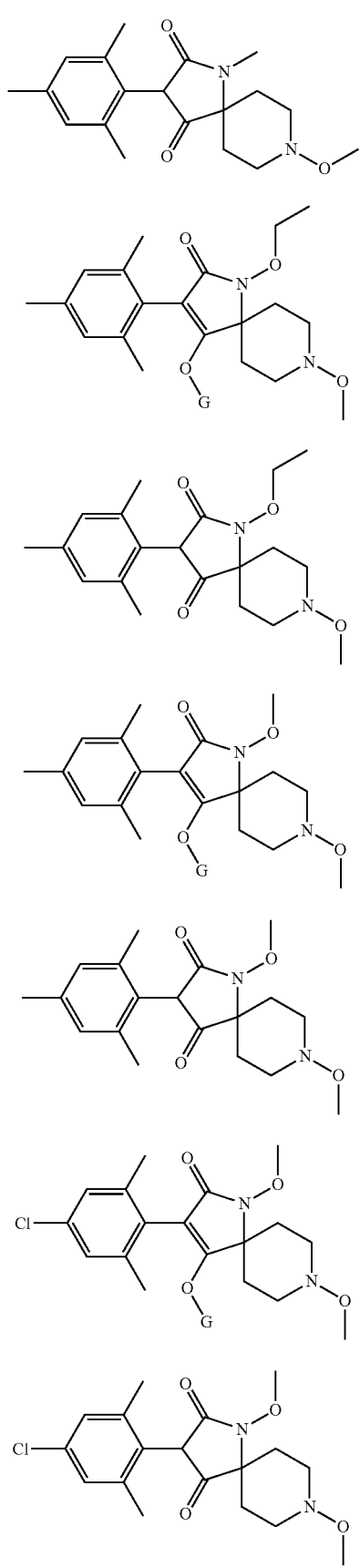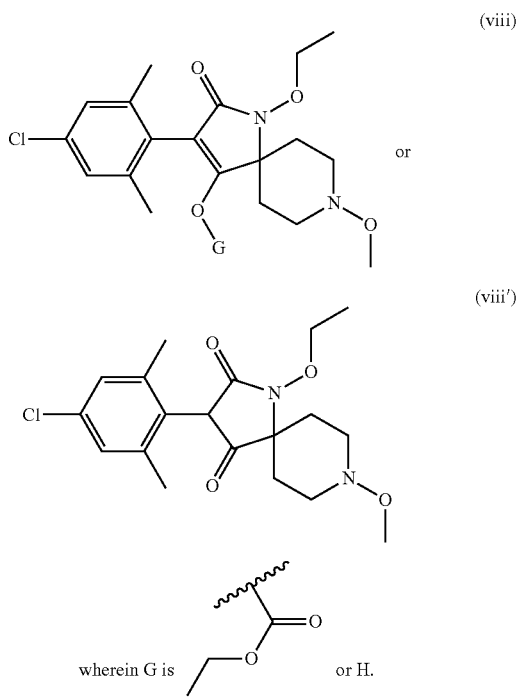
More preferably, the compounds of formula (I') are selected from:
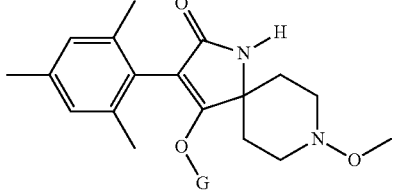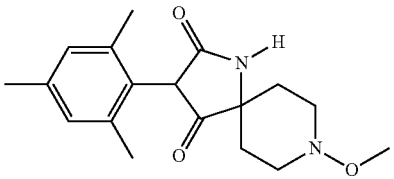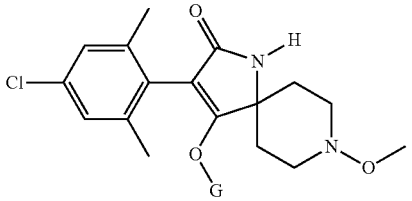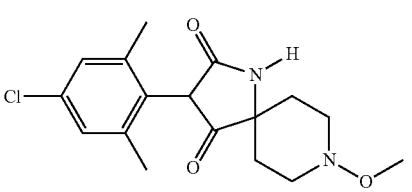

(iii) 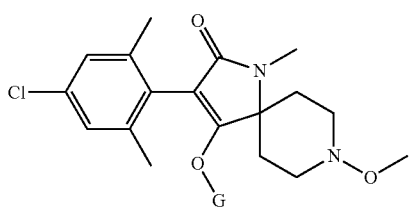

(iii') 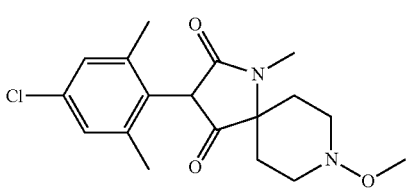

(iv) 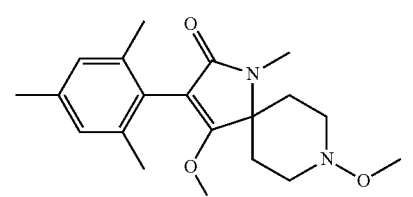

(iv') 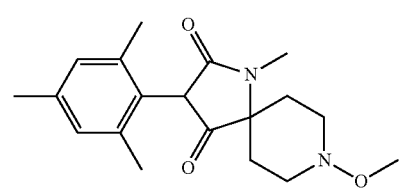

(v) 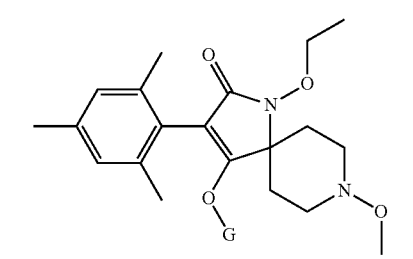

(v') 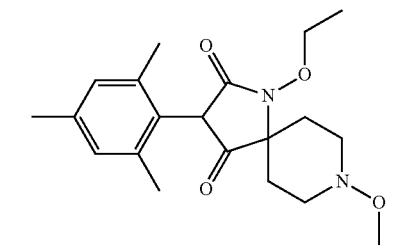

(vi) 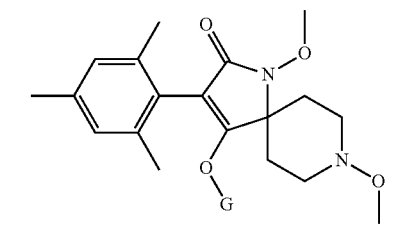

(vi') 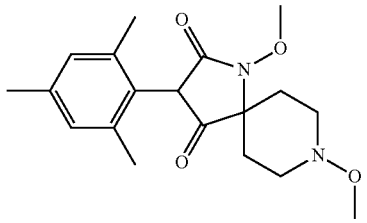

(vii) 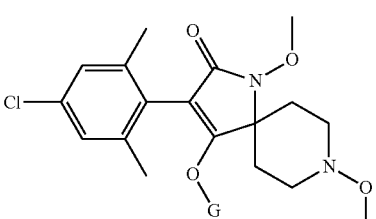

(vii') 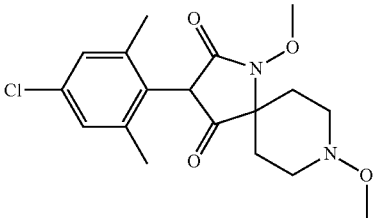

(viii) 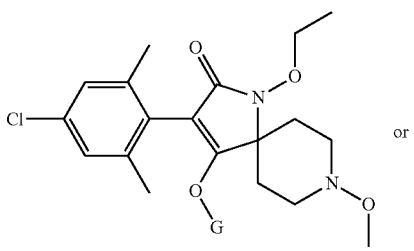

or (viii') 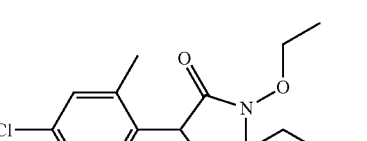

wherein G is 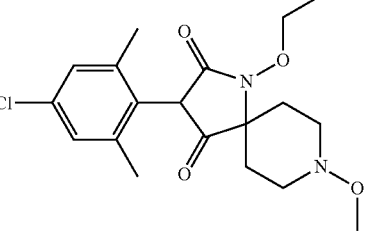

In one embodiment of the invention the first composition with nematicidal properties is applied to a seed and also a first composition is applied to the soil surrounding a planted seed or plant, wherein the first composition applied to the seed is the same as or different from the first composition applied to the soil surrounding a planted seed or plant.

The method according the invention covers the embodiment wherein the first composition comprises a chemical nematicide. The chemical nematicide is preferably selected from the group of known chemical nematicides consisting of 1,2-dibromo-3-chloropropane, 1,2-dichloropropane, 1,2-dichloropropane with 1,3-dichloropropene, 1,3-dichloropropene, 3,4-dichlorotetrahydrothiophene 1,1-dioxide, 3-(4-chlorophenyl)-5-methylrhodanine, 5-methyl-6-thioxo-1,3,5-thiadiazinan-3-ylacetic acid, 6-isopentenylaminopurine, abamectin, acetoprole, alanycarb, aldicarb, aldoxycarb, benclothiaz, benomyl, butylpyridaben, cadusafos, carbofuran, carbon disulfide, carbosulfan, chloropicrin, chlorpyrifos, cloethocarb, cytokinins, dazomet, DBCP, DCIP, diamidafos, dichlofenthion, dicliphos, dimethoate, doramectin, emamectin, emamectin benzoate, eprinomectin, ethoprophos, ethylene dibromide, fenamiphos, fenpyrad, fensulfothion, fluensulfone, fosthiazate, fosthietan, furfural, GY-81, heterophos, imicyafos, imicyafos, iodomethane, isamidofos, isazofos, ivermectin, kinetin, mecarphon, metam, metam-potassium, metam-sodium, methyl bromide, methyl isothiocyanate, milbemycin oxime, moxidectin, *Myrothecium verrucaria* composition, oxamyl, oxamyl carbamate, phorate, phosphamidon, phosphocarb, sebufos, selamectin, spinosad, terbam, terbufos, tetrachlorothiophene, thiafenox, thionazin, triazophos, triazuron, xylenols, YI-5302 and zeatin. Said chemical nematicides can be applied to the seed or to the soil surrounding the planted seed or plant arising from the seed or to both the seed and the soil. Said chemical nematicide applied to the seed can be different from the chemical nematicide applied to the soil.

In the case that the chemical nematicide is applied to the seed it is applied at a rate of 0.05 to 2.0 mg/seed, preferably 0.10 to 1.0 mg/seed, more preferably 0.15 to 0.5 mg/seed, most preferably 0.15 to 0.30 mg/seed. Preferably, it is only applied to the seed.

In the case that the chemical nematicide is applied to the soil surrounding the planted seed or plant it is applied at a rate of 0.05 to 2.0 mg/seed, preferably 0.10 to 1.0 mg/seed, more preferably 0.15 to 0.5 mg/seed, most preferably 0.15 to 0.30 mg/seed. Preferably, it is only applied to the soil surrounding the planted seed or plant.

In the case that the chemical nematicide is applied to the seed and to the soil surrounding the seed or plant it is applied at a rate of 0.05 to 2.0 mg/seed, preferably 0.10 to 1.0 mg/seed, more preferably 0.15 to 0.5 mg/seed, most preferably 0.15 to 0.30 mg/seed to the seeds and a rate of 1 to 1000 g/ha, preferably 1 to 500 g/ha, more preferably 10 to 400 g/ha, most preferably 30 to 400 g/ha.

Preferably, the first composition comprises a chemical nematicide selected from one or more of abamectin, fosthiazate or oxamyl carbamate. Said chemical nematicides can be applied to the seed or to the soil surrounding the planted seed or plant arising from the seed or to both the seed and the soil. Preferably the chemical nematicides are applied only to the seed.

Preferably, the first composition comprises the chemical nematicide abamectin, which can be applied to the seed or to the soil surrounding the planted seed or plant or both to the seed and to the soil surrounding the planted seed or plant. In one embodiment abamectin is applied only to the seeds.

In the case that abamectin is applied only to the seed it is applied at a rate of 0.1 to 1.0 mg active ingredient/seed, preferably 0.1 to 0.6 mg/seed, more preferably 0.1 to 0.3 mg/seed, most preferably 0.15 to 0.3 mg/seed.

In the case that abamectin is applied only to the soil surrounding the planted seed or plant it is applied at a rate of 0.1 to 1.0 mg active ingredient/seed, preferably 0.1 to 0.6 mg/seed, more preferably 0.1 to 0.3 mg/seed, most preferably 0.15 to 0.3 mg/seed.

In the case that abamectin is applied to the seed and to the soil surrounding the seed or plant it is applied at a rate of 0.050 to 1.0 mg/seed, preferably 0.05 to 0.30 mg/seed, more preferably 0.10 to 0.30 mg/seed, most preferably 0.15 to 0.25 mg/seed to the seeds and a rate of 1 to 1000 g/ha, preferably 1 to 500 g/ha, more preferably 10 to 400 g/ha, most preferably 30 to 400 g/ha to the soil surrounding the seed or plant of the seed.

The first composition may comprise a biological nematicide instead of (or in addition to) the chemical nematicide. The biological nematicide is preferably selected from the group of known biological nematicides consisting of *Myrothecium verrucaria, Burholderia cepacia, Bacillus chitonosporus, Paecilomyces lilacinus, Bacillus amyloliquefaciens, Bacillus firmus, Bacillus subtillis, Bacillus pumulis*, and *Pasteuria* spp., preferably *Pasteuria nishizawae* strain Pn1 and *Pasteuria usgae.*

The first composition, or the second composition, or both the first composition and the second composition, may further comprise at least one insecticide or fungicide in addition to the nematicide.

When it is stated herein that the first application is applied to the "soil" surrounding the planted seed or plant produced from said seed, by this is meant several methods of application of the compound directly to the soil. This can be a drench application or a drip application. The drip application can be applied via an irrigation system.

i) applying a first composition with nematicidal properties to a seed and/or to the soil surrounding a planted seed or plant;
ii) and applying a second composition comprising a systemic nematicidal compound to an aerial plant part of said plant or plant produced from the seed;

The invention also covers a method to combat and control nematodes comprising at least two treatments, namely:

i) applying a first composition comprising abamectin to a seed prior to planting and/or to the soil surrounding a planted seed or plant;
ii) and applying a second composition comprising a systemic nematicidal compound to an aerial plant part of said previously treated plant or plant produced from said previously treated seed;

wherein the systemic nematicidal compound is selected from a compound according to one or more of formula (i) and (i') to (viii) to (viii').

Preferably, in step (i), the first composition comprising abamectin is applied to the seed prior to planting.

In a preferred embodiment, the plants treated are in need of protection from nematodes, in particular phytoparasitic nematodes.

EXAMPLES

In the examples below:

Compound A is:

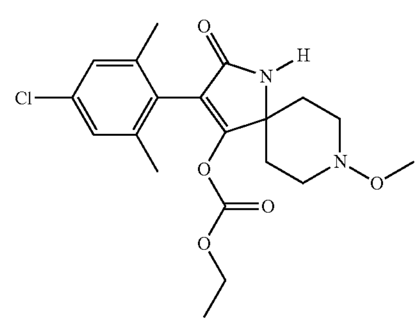 [SMILES: CCOC(=O)OC1=C(c2c(C)cc(Cl)cc2C)C(=O)NC12CCN(OC)CC2]

and Compound B is:

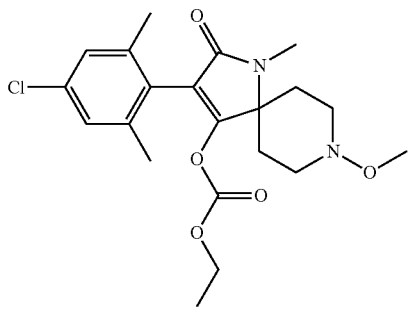 [SMILES: CCOC(=O)OC1=C(c2c(C)cc(Cl)cc2C)C(=O)N(C)C12CCN(OC)CC2]

Example 1

Solo Use of the Compound According to Formula (I)

POT TRIALS: Foliar spray in Cotton against nematodes *Meloidogyne incognita* (RKNi) using
Trial Design and Layout:

12 1-L Clay pots were used per treatment. Cotton: Fibre Max 966 seeds were planted into pots and allowed to germinate and grow into young plants. The pots were artificially infested with nematodes (RKNi) 2 days after treatment.

APPLICATION: Compounds A and B and comparison Spirotetramat were sprayed as a normal foliar spray with hollow cone nozzles directed onto the plants. The compounds A, B and spirotetramat used were formulated as a suspension concentrate formulation at a dose rate of 100 g/ha. The compounds were diluted to a spray volume of approx 150l/ha, which was used on the young plants. The treatment was applied when the plants had at least 2 true leaves.

Industry comparison Abamectin as a seed treatment was also included in the trials as a comparison. AVICTA® 500 FS from Syngenta AG was used at a rate of 500 g/L as a flowable concentrate (FS) formulation and applied to the seeds as a slurry to provide a rate of 0.15 mg of active ingredient per seed.

ASSESSMENT: Plants were removed 2 days after foliar spray treatment to assess penetration of the nematode in the roots with a dyeing method. Root galling/cysts were assessed according to standard practice.

TABLE I

Artificial infestation with nematodes 2 days after foliar spray (at crop stage BBCH 14)

| Product | Dose rate | Application type | Crop stage at application | % root length in cm compared to check (= 100%) | Number of root galls per plant |
|---|---|---|---|---|---|
| Check | | | | 100 | 3.5 |
| Comparison: Abamectin | 0.15 mg/seed | seed treatment | BBCH 00 | 211 | 0.33 |
| Invention: Compound A | 100 g/ha | foliar | BBCH 14 | 204 | 1 |
| Invention: Compound B | 100 g/ha | foliar | BBCH 14 | 213 | 0.33 |

TABLE I-continued

Artificial infestation with nematodes 2 days after foliar spray (at crop stage BBCH 14)

| Product | Dose rate | Application type | Crop stage at application | % root length in cm compared to check (= 100%) | Number of root galls per plant |
|---|---|---|---|---|---|
| Comparison: Spirotetramat | 100 g/ha | foliar | BBCH 14 | 100 | 5.83 |

The longer the roots, the more effective the treatment. The lower the number of root galls per plant the more effective the treatment.

Thus, it was observed that Compounds A and B used according to the invention provided similar control against nematodes in comparison to the industry standard AVICTA® (i.e. Abamectin used as a seed treatment). In comparison to prior art tetramic acid compounds, Compounds A and B outperformed spirotetramat.

Example 2

Synergistic Use of a First Composition Comprising a Nematicide with a Second Composition Comprising Compound A According to Formula (I')

POT TRIALS: Seed treatments and Foliar spray in sugar beets (Beta Vulgaris cv Impulse) against root nematodes *Heterodera schachtii* Schmidt (SBCN) (origin Münster, Germany)
Trial Design and Layout:

15 7-L pots were used per treatment containing 7-L soil with an organic matter content of 2% (drench soil+sand). Seeds were planted into pot soil 1 cm deep and allowed to germinate and grow into young plants in a polytunnel. During the winter months, the pots were placed in a greenhouse. The pots were artificially infested with nematodes (SBCN) when preparing the soil for each pot and just before planting.

APPLICATION: Compounds A and comparison Spirotetramat were sprayed as a normal foliar spray with hollow cone nozzles directed onto the plants. The compounds A and Spirotetramat used were formulated as a suspension concentrate formulation at a dose rate of 100 g/ha. The first foliar spray was applied 14 days after sowing. A second foliar spray was carried out 3 weeks later.

Abamectin was used as a seed treatment. AVICTA® 500 FS from Syngenta AG was used at a rate of 500 g/L as a flowable concentrate (FS) formulation and applied to the seeds as a slurry to provide a rate of 0.6 mg of active ingredient per seed.

ASSESSMENT: Sugar beet plants were harvested after 4 months according to the prevailing temperatures and weather conditions. Sugar beet tuber weights were assessed according to standard practice.

TABLE II

Mean tuber weight relative to inoculated check (%); n = 8-10

| | Dose rate of AI | Timing of first application | Application type | Observed % | Expected % |
|---|---|---|---|---|---|
| Abamectin (Avicta® 500 FS) | 0.6 mg/seed | At sowing | Seed treatment | 6.4 | |

TABLE II-continued

Mean tuber weight relative to inoculated check (%); n = 8-10

| | Dose rate of AI | Timing of first application | Application type | Observed % | Expected % |
|---|---|---|---|---|---|
| Invention: Compound A (SC100) | 100 g/ha | +14 days after sowing | Foliar | 17.0 | |
| Invention: Abamectin (Avicta ® 500 FS) + Compound A (SC100) | 0.6 mg/ seed + 100 g/ha | At sowing + 14 days after sowing | Seed treatment + Foliar | 48.3 | 22.3 |
| Comparison: Spirotetramat (Movento ® SC 100) | 100 g/ha | +14 days after sowing | Foliar | 30.0 | |
| Comparison: Abamectin (Avicta ® 500 FS) + Spirotetramat (Movento ® SC 100) | 0.6 mg/ seed + 100 g/ha | At sowing + 14 days after sowing | Seed treatment + Foliar | −6.2 | 34.5 |

This trial showed that the applied test method was appropriate for evaluation of damage caused by the sugar beet cyst nematode *Heterodera schachtii* over a longer period of time. There were distinct differences between the infected and uninfected plants in both weight and visual assessments.

In combination with an effective seed treatment (Avicta® standard), the compound according to the invention showed that the root tuber weight was significantly increased over the infested control and Avicta® alone, much more than expected. In view of an integrated crop strategy applying a seed treatment nematicide to sugar beet and following up with foliar sprays of the compound of formula (I') could be an attractive management program for long term nematode control over an entire growing season. The same synergy could not be observed in the combination of an abamectin seed treatment (Avicta®) with spirotetramat (Movento®).

Example 3

Synergistic Use of a First Composition Comprising a Nematicide with a Second Composition Comprising Compound B According to Formula (I')

POT TRIALS: Seed treatments and Foliar spray in sugar beets (Beta Vulgaris cv Impulse) against root nematodes *Heterodera schachtii* Schmidt (SBCN)

Trial Design and Layout:

8×350 ml pots were used per treatment containing 350 ml soil (70% drench soil and 30% sand). 1 Seed per pot were planted into pot soil 0.5 cm deep and allowed to germinate and grow into young plants. Plants were kept under constant conditions of 25° C. during the day and 23° C. during the night with a humidity of 50-60% with 14 hour light periods. The pots were artificially infested with nematodes (SBCN) 7 days after sowing. For inoculation, 3 holes are drilled into the soil and 2 ml suspension of the nematodes per hole are applied.

APPLICATION: Compounds B and comparison Spirotetramat were sprayed as a normal foliar spray with hollow cone nozzles directed onto the plants. The compounds B and Spirotetramat used were formulated as a suspension concentrate formulation at a dose rate of 100 g/ha. The first foliar spray was applied 14 days after sowing (i.e. 7 days after inoculation). A second foliar spray was carried out 21 days after sowing (i.e. 14 days after inoculation).

Abamectin was used as a seed treatment. AVICTA® 400 FS from Syngenta AG was used at a rate of 400 g/L as a flowable concentrate (FS) formulation and applied to the seeds as a slurry to provide a rate of 0.6 mg and 1 mg of active ingredient per seed.

ASSESSMENT: Sugar beet plants were harvested 25 days after inoculation. Sugar beet root and shoot weights were assessed according to standard practice. Number of cysts per root system and as a function of root weight were assessed.

TABLE III

Efficacy in % of cyst nematodes per root system at rate of Abamectin 1 mg/seed

| Treatment | Abamectin 1 mg/seed | Compound B 100 g/ha | Expected Abamectin 1 mg/ seed + Compound B 100 g/ha | Observed Abamectin 1 mg/ seed + Compound B 100 g/ha | Synergy? |
|---|---|---|---|---|---|
| Efficacy in % | 60% | 12% | 71% | 82% | yes |

TABLE IV

Efficacy in % of cyst nematodes per root system at rate of Abamectin 0.6 mg/seed

| Treatment | Abamectin 0.6 mg/ seed | Compound B 100 g/ha | Expected Abamectin 1 mg/ seed + Compound B 100 g/ha | Observed Abamectin 1 mg/ seed + Compound B 100 g/ha | Synergy? |
|---|---|---|---|---|---|
| Efficacy in % | 42% | 12% | 54% | 59% | yes |

This test showed that a combined application of Compound B together with Abamectin applied according to the invention has a synergistic effect against the reproduction of *H. schachtii* on sugarbeet. It can be seen that the number of developed females was reduced by more than the Colby formula would let expect from the solo treatments. Therefore, synergy is proven.

The invention claimed is:

1. A method of controlling nematodes in the soil of crop plants, comprising applying to the crop plants a compound according to formula (iii)

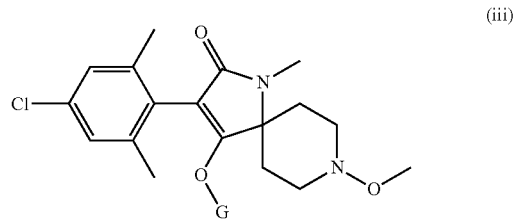

(iii)

wherein
- G is hydrogen or a latentiating group selected from —C(=O)—$R^a$ or —C(=O)—O—$R^b$; wherein $R^a$ is selected from hydrogen, $C_1$-$C_{12}$alkyl, $C_2$-$C_{12}$alkenyl, $C_2$-$C_{12}$alkynyl, $C_1$-$C_{10}$haloalkyl and $R^b$ is selected from $C_1$-$C_{12}$alkyl, $C_2$-$C_{12}$alkenyl, $C_2$-$C_{12}$alkynyl and $C_1$-$C_{10}$haloalkyl;
- or an agrochemically acceptable salt or an N-oxide thereof.

2. The method according to claim 1 for combating and controlling phytoparasitic nematodes.

3. The method according to claim 1 for combating and controlling nematodes in perennial or annual crops.

4. The method according to claim 1 for combating and controlling nematodes in the group consisting of vegetables, citrus, grapes or mixtures thereof.

5. The method according to claim 1 wherein the compounds of the formula (iii) as defined according to claim 1 are applied to the crops as a foliar treatment.

\* \* \* \* \*